United States Patent
Zhang et al.

(10) Patent No.: US 11,945,125 B2
(45) Date of Patent: Apr. 2, 2024

(54) AUXILIARY PHOTOGRAPHING DEVICE FOR DYSKINESIA ANALYSIS, AND CONTROL METHOD AND APPARATUS FOR AUXILIARY PHOTOGRAPHING DEVICE FOR DYSKINESIA ANALYSIS

(71) Applicant: TENCENT TECHNOLOGY (SHENZHEN) COMPANY LIMITED, Shenzhen (CN)

(72) Inventors: Lin Zhang, Shenzhen (CN); JianBao Wu, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 392 days.

(21) Appl. No.: 17/475,677

(22) Filed: Sep. 15, 2021

(65) Prior Publication Data
US 2022/0001544 A1 Jan. 6, 2022

Related U.S. Application Data

(63) Continuation of application No. PCT/CN2020/113755, filed on Sep. 7, 2020.

(30) Foreign Application Priority Data

Sep. 16, 2019 (CN) .......................... 201910873009.6

(51) Int. Cl.
*B25J 9/16* (2006.01)
*A61B 5/00* (2006.01)
(Continued)

(52) U.S. Cl.
CPC .......... *B25J 9/1697* (2013.01); *A61B 5/1116* (2013.01); *A61B 5/4082* (2013.01); *B25J 9/023* (2013.01); *B25J 19/023* (2013.01)

(58) Field of Classification Search
CPC .......... B25J 9/023; B25J 9/1697; B25J 19/023
See application file for complete search history.

(56) References Cited

U.S. PATENT DOCUMENTS

| | | | |
|---|---|---|---|
| 7,274,803 B1 * | 9/2007 | Sharma | G06V 40/107 382/128 |
| 2011/0102568 A1 | 5/2011 | Bonnet | |
| 2016/0271803 A1 | 9/2016 | Stewart | |

FOREIGN PATENT DOCUMENTS

| | | |
|---|---|---|
| CN | 102662410 A | 9/2012 |
| CN | 102831380 A | 12/2012 |

(Continued)

OTHER PUBLICATIONS

English WIPO translation of CN-107564065-A. (Year: 2018).*

(Continued)

*Primary Examiner* — Jason Holloway
*Assistant Examiner* — Christopher A Buksa
(74) *Attorney, Agent, or Firm* — Crowell & Moring LLP

(57) ABSTRACT

The present disclosure relates to the field of artificial intelligence (AI) technologies, and provides an auxiliary photographing device for dyskinesia analysis, and a control method and apparatus for an auxiliary photographing device for dyskinesia analysis. The method includes controlling a camera assembly of the auxiliary photographing device at a first position to perform photographing, to obtain a first image, the first image comprising a target body part of a patient having dyskinesia; determining, in the first image, a position of a target region corresponding to the target body part; controlling an orientational movement of a mechanical arm of the auxiliary photographing device according to the position of the target region, to adjust the camera assembly to a second position; and controlling the camera assembly at the second position to perform photographing, to obtain a (Continued)

second image, the second image comprising the target body part.

18 Claims, 21 Drawing Sheets

(51) Int. Cl.
    *A61B 5/11*     (2006.01)
    *B25J 9/02*     (2006.01)
    *B25J 19/02*     (2006.01)

(56) References Cited

FOREIGN PATENT DOCUMENTS

| | | | |
|---|---|---|---|
| CN | 105937692 | A | 9/2016 |
| CN | 107016667 | A | 8/2017 |
| CN | 107564065 | A * | 1/2018 |
| CN | 108647633 | A | 10/2018 |
| CN | 108734065 | A | 11/2018 |
| CN | 108734066 | A | 11/2018 |
| CN | 109717833 | A | 5/2019 |
| CN | 109859324 | A | 6/2019 |
| CN | 110561399 | A | 12/2019 |
| JP | 2007-260404 | A | 10/2007 |
| JP | 2019-150533 | A | 9/2019 |

OTHER PUBLICATIONS

Japanese Office Action with English translation regarding JP 2021-559634 dated Aug. 31, 2020, 10 pages.
International Search Report with English translation and Written Opinion regarding PCT/CN2020/113755 dated Dec. 9, 2020.
Chinese Office Action with English concise explanation regarding CN201910873009.6 dated May 25, 2021.
Xinan Li, "Kinect-based gait anomalies detection," published on Jan. 15, 2017 in Chinese Master's Theses Full-text Database with concise description, Information Science and Technology, vol. 1.
Extended European Search Report regarding EP 20 86 6517 dated Jul. 25, 2022, 10 pages.
Rosenstrauch Martin J. et al: "Human robot collaboration—using kinect v2 for ISO/TS 15066 speed and separation monitoring," Procedia CIRP, vol. 76, Dec. 31, 2018, pp. 183-186.
Bruno Siciliano et al: "Visual Servoing" In: "Robotics : modelling, planning and Control," Dec. 31, 2009, Springer, UK, XP055460541, ISBN: 978-1-84628-641-4, pp. 407-467.
Babaians Edwin et al: "Skeleton and visual tracking fusion for human following task of service robots," 2015 3rd RSI International Conference on Robotics and Mechatronics (ICROM), IEEE, Oct. 7, 2015, pp. 761-766.
Second Japanese Office Action with English translation regarding JP 2021-559634 dated Dec. 27, 2022, 5 pages.

* cited by examiner

AUXILIARY PHOTOGRAPHING DEVICE FOR DYSKINESIA ANALYSIS, AND CONTROL METHOD AND APPARATUS FOR AUXILIARY PHOTOGRAPHING DEVICE FOR DYSKINESIA ANALYSIS

RELATED APPLICATION

This application is a continuation application of PCT Patent Application No. PCT/CN2020/113755, filed on Sep. 7, 2020, which claims priority to Chinese Patent Application No. 201910873009.6, filed with the China National Intellectual Property Administration on Sep. 16, 2019, both of which are incorporated herein by reference in their entireties.

FIELD OF THE TECHNOLOGY

Embodiments of this application relate to the field of artificial intelligence (AI) technologies, and in particular, to an auxiliary photographing device for dyskinesia analysis, and a control method and apparatus for an auxiliary photographing device for dyskinesia analysis.

BACKGROUND OF THE DISCLOSURE

As science and technology develop, a diagnosis of dyskinesia (such as Parkinson disease) no longer completely depends on visual inspection of medical workers. Instead, some devices, such as wearable devices may be used for performing a quantitative diagnosis.

In the related art, dyskinesia is detected by using a sensor. For example, the sensor may be installed in a wearable device (such as gloves). A patient wears the wearable device, and performs a corresponding action. The sensor built in the wearable device acquires motion data in real time. Medical workers may diagnose the patient according to the acquired motion data.

In the related art, the wearable device worn by the patient may affect the action of the patient, resulting in data distortion. As a result, an analysis result is inaccurate.

The present disclosure describes embodiments for controlling an auxiliary photographing device for dyskinesia analysis, addressing at least one of the problems/issues discussed above, improving data authenticity and/or improving the accuracy of an analysis result.

SUMMARY

Embodiments of this application provide an auxiliary photographing device for dyskinesia analysis, and a control method and apparatus for an auxiliary photographing device for dyskinesia analysis, which can improve data authenticity, thereby improving the accuracy of an analysis result. The various embodiments in the present disclosure includes technical solutions.

The present disclosure describes an apparatus for controlling an auxiliary photographing device for dyskinesia analysis. The apparatus includes a memory storing instructions; and a processor in communication with the memory. When the processor executes the instructions, the processor is configured to cause the apparatus to perform: controlling a camera assembly of the auxiliary photographing device at a first position to perform photographing, to obtain a first image, the first image comprising a target body part of a patient having dyskinesia, determining, in the first image, a position of a target region corresponding to the target body part, controlling an orientational movement of a mechanical arm of the auxiliary photographing device according to the position of the target region, to adjust the camera assembly to a second position, and controlling the camera assembly at the second position to perform photographing, to obtain a second image, the second image comprising the target body part.

The present disclosure describes a method for controlling an auxiliary photographing device for dyskinesia analysis. The method includes controlling, by a device, a camera assembly of the auxiliary photographing device at a first position to perform photographing, to obtain a first image, the first image comprising a target body part of a patient having dyskinesia. The device includes a memory storing instructions and a processor in communication with the memory. The method also includes determining, by the device in the first image, a position of a target region corresponding to the target body part; controlling, by the device, an orientational movement of a mechanical arm of the auxiliary photographing device according to the position of the target region, to adjust the camera assembly to a second position; and controlling, by the device, the camera assembly at the second position to perform photographing, to obtain a second image, the second image comprising the target body part.

The present disclosure describes a non-transitory computer-readable storage medium, storing computer-readable instructions. The computer-readable instructions, when executed by a processor, are configured to cause the processor to perform: controlling a camera assembly of an auxiliary photographing device at a first position to perform photographing, to obtain a first image, the first image comprising a target body part of a patient having dyskinesia; determining, in the first image, a position of a target region corresponding to the target body part; controlling an orientational movement of a mechanical arm of the auxiliary photographing device according to the position of the target region, to adjust the camera assembly to a second position; and controlling the camera assembly at the second position to perform photographing, to obtain a second image, the second image comprising the target body part.

According to an aspect of the embodiments of this application, an auxiliary photographing device for dyskinesia analysis is provided, the auxiliary photographing device including a base, a mechanical arm, a control assembly, and a camera assembly, one end of the mechanical arm being connected to the base; and the camera assembly being disposed on the mechanical arm, the control assembly being electrically connected to the mechanical arm and the camera assembly, and the control assembly being configured to adjust a position of the camera assembly by controlling an orientational movement of the mechanical arm and control the camera assembly to perform photographing, the orientational movement of the mechanical arm including at least one of a horizontal movement and a vertical movement.

According to an aspect of the embodiments of this application, a control method for an auxiliary photographing device for dyskinesia analysis is provided, applicable to the control assembly in the auxiliary photographing device for dyskinesia analysis described in the foregoing aspect, the method including:

controlling the camera assembly at a first position to perform photographing, to obtain a first image, the first image including a target body part of a patient having dyskinesia;

determining a position, in the first image, of a target region corresponding to the target body part;

controlling the orientational movement of the mechanical arm according to the position, in the first image, of the target region corresponding to the target body part, to adjust the camera assembly to a second position; and controlling the camera assembly at the second position to perform photographing, to obtain a second image, the second image including the target body part.

According to an aspect of the embodiments of this application, a control apparatus for an auxiliary photographing device for dyskinesia analysis is provided, applicable to the control assembly in the auxiliary photographing device for dyskinesia analysis described in the foregoing aspect, the apparatus including:

a photographing control module, configured to control the camera assembly at a first position to perform photographing, to obtain a first image, the first image including a target body part of a patient having dyskinesia;

a position determination module, configured to determine a position, in the first image, of a target region corresponding to the target body part; and a position adjustment module, configured to control an orientational movement of the mechanical arm according to the position of the target region in the first image, to adjust the camera assembly to a second position; and the photographing control module being configured to control the camera assembly at the second position to perform photographing, to obtain a second image, the second image including the target body part.

According to an aspect of the embodiments of this application, a control assembly is provided, including a processor and a memory, the memory storing at least one instruction, at least one program, a code set, or an instruction set, the at least one instruction, the at least one program, the code set, or the instruction set being loaded and executed by the processor to perform the control method for the auxiliary photographing device for dyskinesia analysis described in the foregoing aspect.

According to an aspect of the embodiments of this application, a computer-readable storage medium is provided, storing at least one instruction, at least one program, a code set, or an instruction set, the at least one instruction, the at least one program, the code set, or the instruction set being loaded and executed by a processor to perform the control method for the auxiliary photographing device for dyskinesia analysis described in the foregoing aspect.

According to an aspect of the embodiments of this application, a computer program product is provided, the computer program product, when executed by a processor, being used for implementing the control method for the auxiliary photographing device for dyskinesia analysis described in the foregoing aspect.

The technical solutions provided in the embodiments of this application may include the following beneficial effects:

The embodiments of this application provide an auxiliary photographing device for dyskinesia analysis. The control assembly in the auxiliary photographing device can adjust the position of the camera assembly by controlling the orientational movement of the mechanical arm and control the camera assembly to perform photographing. In the related art, a patient is required to wear a wearable device to obtain motion data of the patient. By virtue of the auxiliary photographing device provided in the embodiments of this application, a patient is required to wear no devices, which reduces a constraint on a motion of the patient, thereby ensuring data authenticity, and further improving the accuracy of analysis and diagnosis results.

DESCRIPTION OF EMBODIMENTS

Figure 1:
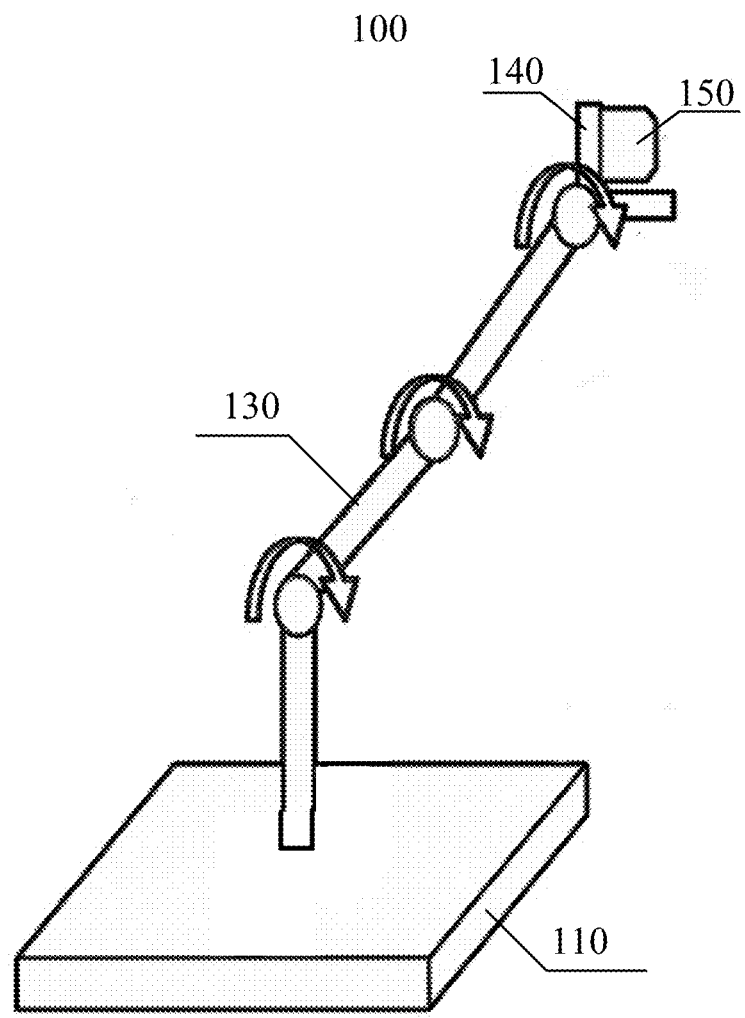
FIG. 1 is a schematic diagram of an auxiliary photographing device for dyskinesia analysis according to an embodiment of this application.

To make objectives, technical solutions, and advantages of this application clearer, the following further describes implementations of this application in detail with reference to the accompanying drawings.

Artificial Intelligence (AI) is a theory, method, technology, and application system that use a digital computer or a machine controlled by a digital computer to simulate, extend, and expand human intelligence, perceive the environment, obtain knowledge, and use the knowledge to obtain the best result. In other words, AI is a comprehensive technology of computer science, which attempts to understand essence of intelligence and produces a new intelligent machine that responds in a manner similar to human intelligence. AI is to study the design principles and implementation methods of various intelligent machines, to enable the machines to have the functions of perception, reasoning, and decision-making.

The AI technology is a comprehensive discipline and relates to a wide range of fields including both hardware-level technologies and software-level technologies. The basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning (ML)/deep learning.

The CV is a science that studies how to use a machine to "see", and furthermore, that uses a camera and a computer to replace human eyes to perform machine vision such as recognition, tracking, and measurement on a target, and further perform graphic processing, so that the computer processes the target into an image more suitable for human eyes to observe, or an image transmitted to an instrument for detection. As a scientific discipline, the CV studies related theories and technologies and attempts to establish an AI system that can obtain information from images or multi-dimensional data. The CV technologies generally include technologies such as image processing, image recognition, image semantic understanding, image retrieval, optical character recognition (OCR), video processing, video semantic understanding, video content/behavior recognition, three-dimensional object reconstruction, a 3D technology, virtual reality, augmented reality, synchronous positioning, and map construction, and further include biometric feature recognition technologies such as common face recognition and fingerprint recognition.

Key technologies of the speech technology include an automatic speech recognition (ASR) technology, a text-to-speech (TTS) technology, and a voiceprint recognition technology. To make a computer capable of listening, seeing, speaking, and feeling is the future development direction of human-computer interaction, and speech has become one of the most promising human-computer interaction methods in the future.

Machine Learning (ML) is a multi-field interdiscipline, and relates to a plurality of disciplines such as the probability theory, statistics, the approximation theory, convex analysis, and the algorithm complexity theory. The ML specializes in studying how a computer simulates or implements a human learning behavior to obtain new knowledge or skills, and reorganize an existing knowledge structure, so as to keep improving performance of the computer. The ML is the core of the AI, is a basic way to make the computer intelligent, and is applied to various fields of AI. The ML and deep learning generally include technologies such as an artificial neural network, a belief network, reinforcement learning, transfer learning, inductive learning, and learning from demonstrations.

With the research and progress of the AI technology, the AI technology is studied and applied in a plurality of fields, such as a common smart home, a smart wearable device, a virtual assistant, a smart speaker, smart marketing, unmanned driving, automatic driving, an unmanned aerial vehicle, a robot, smart medical care, and smart customer service. It is believed that with the development of technologies, the AI technology will be applied in more fields, and play an increasingly important role.

The solutions provided in the embodiments of this application relate to technologies such as the CV, speech technology, ML, and the like of AI, and provide an auxiliary photographing device for dyskinesia analysis and a control method for an auxiliary photographing device for dyskinesia analysis. The auxiliary photographing device and the control method for an auxiliary photographing device are applicable to the following: analysis and research of dyskinesia such as the Parkinson's disease, security and protection to determine whether a person in a picture behaves aggressively and to call the police in time, new retail to determine purchase behaviors of people, gait analysis to evaluate athletes' sports conditions and improve performance, biometric identification for locating and tracking an individual in a space, motion capture in, for example, a dancing game, human-computer interaction to control home appliances, and the like.

FIG. 1 is a schematic diagram of an auxiliary photographing device for dyskinesia analysis according to an embodiment of this application. The auxiliary photographing device 100 may include a base 110, a mechanical arm 130, a control assembly 140, and a camera assembly 150.

The base 110 is configured to support other assemblies of the entire auxiliary photographing device 100. One end of the mechanical arm 130 is connected to the base 110. The end of the mechanical arm 130 may be fixedly connected to the base 110, that is, relative positions of the end of the mechanical arm 130 and the base 110 do not change. Alternatively, the end of the mechanical arm may be movably connected to the base, that is, the relative positions of the end of the mechanical arm 130 and the base 110 may change. In addition, the end of the mechanical arm 130 may be directly connected to the base 110. For example, the end of the mechanical arm 130 is directly connected to the base 110 by means of bonding, welding, insertion, or the like. Alternatively, the end of the mechanical arm may be indirectly connected to the base. For example, the end of the mechanical arm 130 is indirectly connected to the base 110 by using an assembly.

In some implementations, the base 110 may have a certain weight so as to stand on a leveled surface to support the system 100. In other implementations, the base 110 may have a clamp so as to clamp onto another object (e.g., edge of table, mechanical protrusion from a wall) to support the system 100. In other implementations, the base 110 may be fastened to another object (e.g., side of a cabinet, a wall) by one or more fastener (e.g., one or more bolt, one or more screw).

The camera assembly 150 is disposed on the mechanical arm 130. The control assembly 140 is electrically connected to the mechanical arm 130 and the camera assembly 150. The control assembly 140 is configured to adjust a position of the camera assembly 150 by controlling an orientational movement of the mechanical arm 130 and control the camera assembly 150 to perform photographing. The orientational movement of the mechanical arm 130 includes at least one of a horizontal movement and a vertical movement.

In this embodiment of this application, the horizontal movement is a movement in a horizontal direction, such as a forward movement, a backward movement, a leftward movement, a rightward movement, or a movement in other directions on a horizontal plane. The vertical movement is a movement in a vertical direction, such as a vertically upward movement, a vertically downward movement, or the like. The mechanical arm 130 may support only the horizontal movement, or may support only the vertical movement, or may support both the horizontal movement and the vertical movement, which is not limited in this embodiment of this application. In addition, the mechanical arm 130 may perform the vertical movement during the horizontal movement, that is, may perform the horizontal movement and the vertical movement simultaneously, which is not limited in this embodiment of this application.

In some embodiments, a "horizontal" and/or "vertical" direction may be relative to a position of the base 110. When the base 110 is rotated and disposed in another orientation, the horizontal and/or vertical directions of movement of the mechanical arm 130 may be adjusted/oriented according to the orientation of the base 110.

In some embodiments, the mechanical arm 130 is further capable of rotating about a fulcrum or an axis. In this way, the orientational movement of the mechanical arm 130 can be more flexible, so that the position of the camera assembly 150 can be more flexibly and precisely adjusted.

Based on the above, the technical solution provided in this embodiment of this application provides an auxiliary photographing device for dyskinesia analysis. The control assembly in the auxiliary photographing device can adjust the position of the camera assembly by controlling the orientational movement of the mechanical arm and control the camera assembly to perform photographing. In the related art, a patient is required to wear a wearable device to obtain motion data of the patient. By virtue of the auxiliary photographing device provided in the embodiments of this application, a patient is required to wear no devices, which reduces a constraint on a motion of the patient, thereby ensuring data authenticity, and further improving the accuracy of analysis and diagnosis results.

Figure 2:
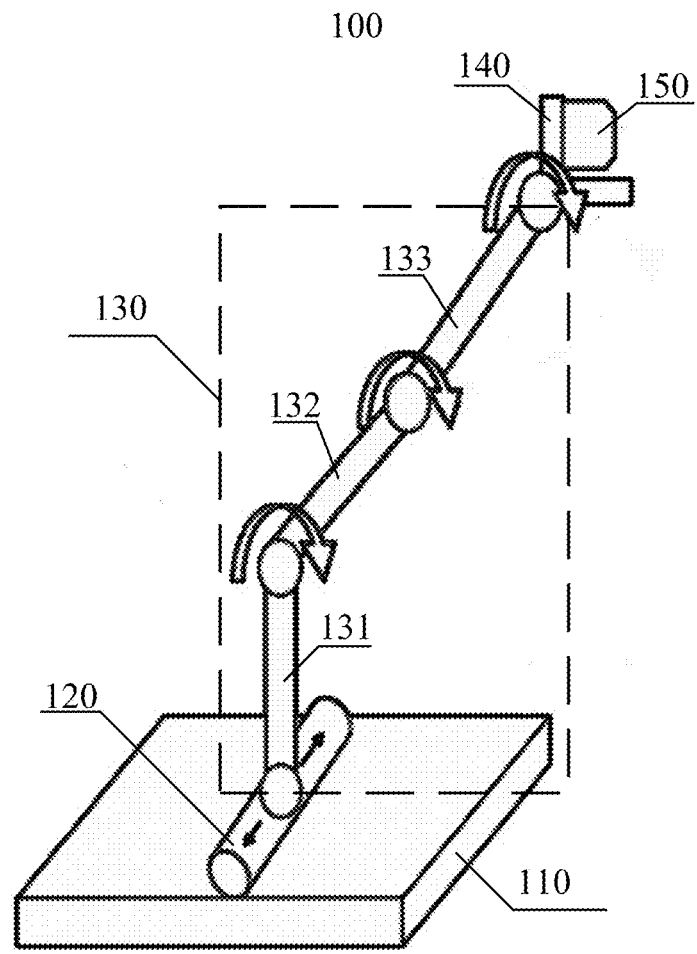
FIG. 2 is a schematic diagram of an auxiliary photographing device for dyskinesia analysis according to another embodiment of this application.

FIG. 2 is a schematic diagram of an auxiliary photographing device for dyskinesia analysis according to another embodiment of this application. The auxiliary photographing device 100 may include a base 110, a translation track 120, a mechanical arm 130, a control assembly 140, and a camera assembly 150.

The base 110 is configured to support other assemblies of the entire auxiliary photographing device 100. The base may be in a regular shape such as a circle, a square, a regular hexagon. or the like, or may be in other irregular shapes, which is not limited in this embodiment of this application. In addition, a material of the base 110 is also not limited in this embodiment of this application.

The translation track 120 is disposed on the base 110. One end of the mechanical arm 130 is disposed on the translation track 120, and the mechanical arm 130 is slidably connected to the translation track 120.

The translation track 120 may be fixedly disposed on the base 110. The end of the mechanical arm 130 may be slidably connected to the translation track 120, so that the end of the mechanical arm 130 is slidable on the translation track.

In some embodiments, the translation track 120 may be a tubular track, and may be connected to the end of the mechanical arm 130 by using a spherical hinge.

In some embodiments, the translation track 120 may be configured to realize a horizontal movement of the mechanical arm 130.

The camera assembly 150 is disposed on the mechanical arm 130. The control assembly 140 is electrically connected to the mechanical arm 130 and the camera assembly 150. The control assembly 140 is configured to adjust a position of the camera assembly 150 by controlling an orientational movement of the mechanical arm 130 and control the camera assembly 150 to perform photographing. The orientational movement of the mechanical arm 130 includes at least one of a horizontal movement and a vertical movement.

The camera assembly 150 may be disposed on another end of the mechanical arm 130, or may be disposed on other positions on the mechanical arm. The position of the camera assembly 150 may be set according to an actual structure of the mechanical arm 130, which is not limited in this embodiment of this application.

The control assembly 140 may include at least one control chip. When the control assembly includes only one control chip, the control chip may control other assemblies to implement various functions, such as photographing, an orientational movement, and the like. When the control assembly includes a plurality of control chips, different control chips may be configured to implement different functions. For example, one control chip is configured to control the camera assembly 150 to perform photographing, another control chip is configured to process an image that is taken, still another control chip is configured to control the orientational movement of the mechanical arm 130, and the like, which is not limited in this embodiment of this application.

In some embodiments, the mechanical arm 130 may perform only the horizontal movement, or may perform only a vertical movement, or may perform both the horizontal movement and the vertical movement, which is not limited in this embodiment of this application.

In some embodiments, the camera assembly 150 includes a zoom lens. The control assembly 140 may control the zoom lens to automatically adjust a focal length as required, to obtain a clearer image. In some other examples, the camera assembly 150 may further include a camera module having a photographing function, such as a digital camera, a digital camera lens, a digital video recorder, or the like, which is not limited in this embodiment of this application.

In this embodiment of this application, according to different structures of the mechanical arm 130, the foregoing auxiliary photographing device 100 may have the following two different designs.

As shown in FIG. 2, a first type of the mechanical arm 130 includes at least two rotary shafts connected to each other, for example, 3 rotary shafts connected to each other, including a first rotary shaft 131, a second rotary shaft 132, and a third rotary shaft 133. A quantity of the rotary shafts may be set according to an actual requirement, which is not limited in this embodiment of this application.

The camera assembly 150 is disposed on the rotary shaft away from the base 110, for example, on one end of the third rotary shaft 133. One end of the rotary shaft 131 is slidably connected to the translation track 120.

The control assembly 140 is configured to adjust a horizontal position of the camera assembly 150 by controlling the mechanical arm 130 to perform the horizontal movement on the translation track 120. The control assembly 140 is configured to adjust a vertical position of the camera assembly 150 by controlling the rotary shaft to perform the vertical movement.

Figure 3:
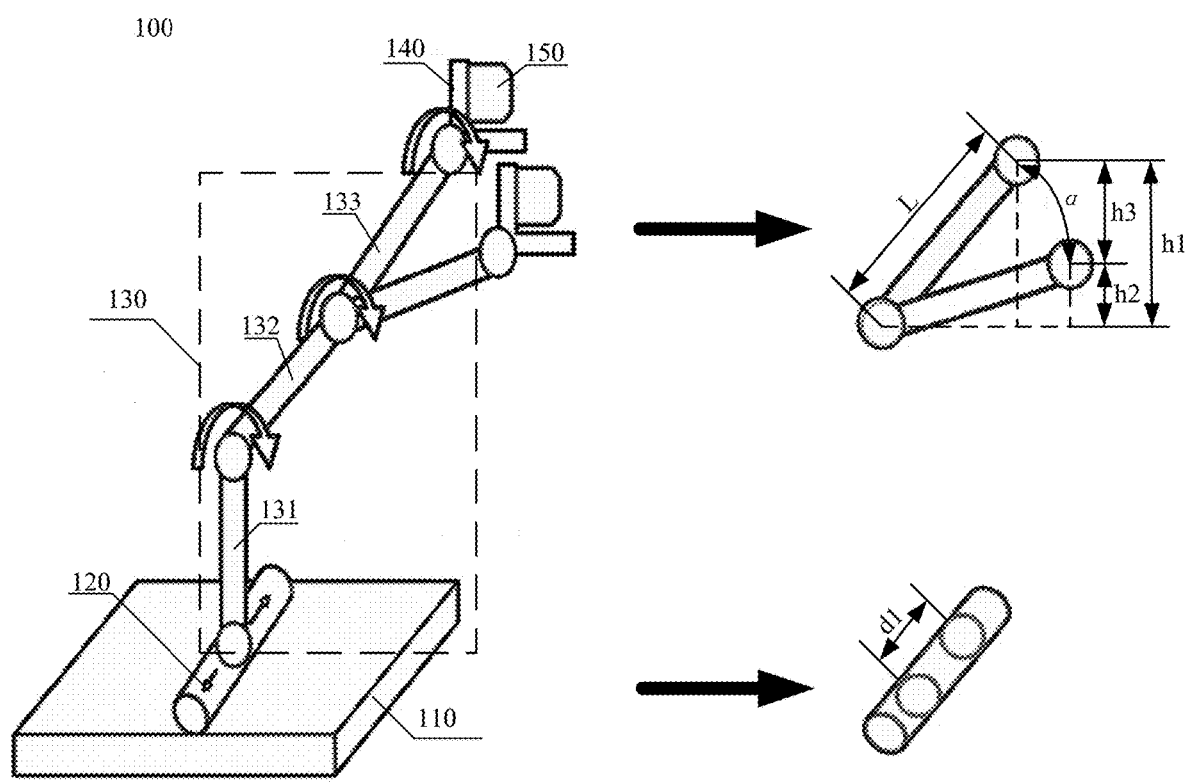
FIG. 3 is an exemplary schematic diagram of an orientational movement of a mechanical arm according to this application.

FIG. 3 is an exemplary schematic diagram of an orientational movement of a mechanical arm. When the control assembly 140 learns from processing that the mechanical arm 130 needs to be horizontally moved by a distance d1 and vertically moved by a distance h3, the control assembly 140 may control the first rotary shaft 131 of the mechanical arm 130 to move on the translation track 120 by the distance d1 and control the third rotary shaft 133 of the mechanical arm 130 to vertically move by the distance h3.

Figure 4:
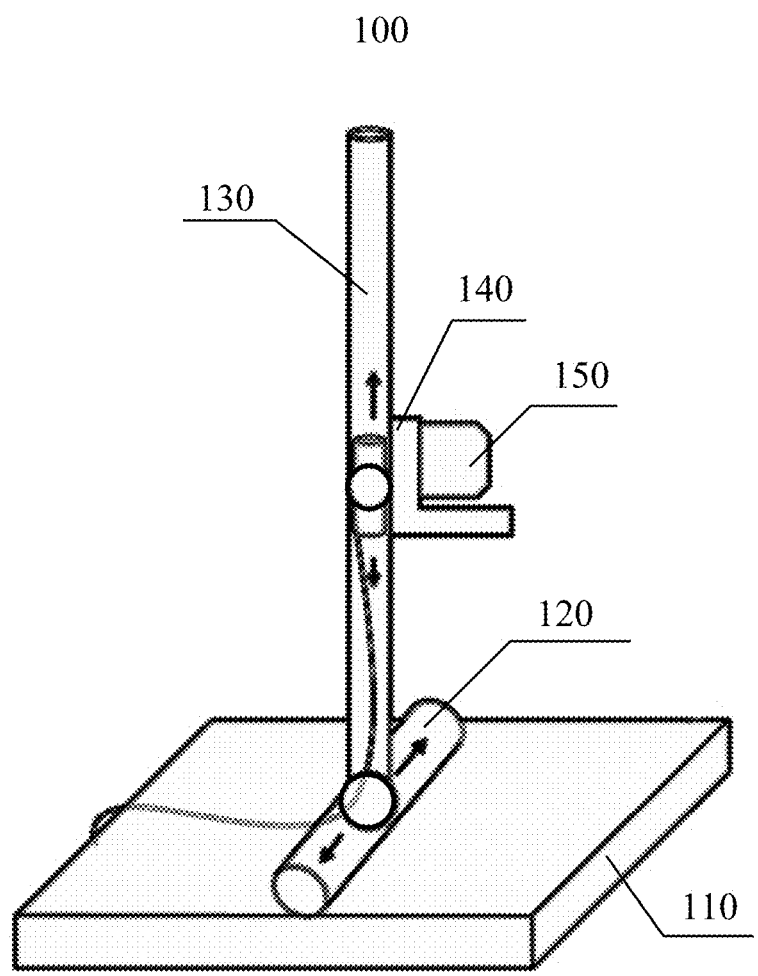
FIG. 4 is an exemplary schematic diagram of another auxiliary photographing device for dyskinesia analysis according to an embodiment of this application.

As shown in FIG. 4, a second type of mechanical arm 130 includes a vertical track. In some embodiments, the vertical track and the translation track 120 form a cross structure.

The control assembly 140 is configured to adjust the horizontal position of the camera assembly 150 by controlling the vertical track of the mechanical arm 130 to perform the horizontal movement on the translation track 120. The control assembly 150 is further configured to control the camera assembly 150 to perform the vertical movement on the vertical track.

Figure 5:
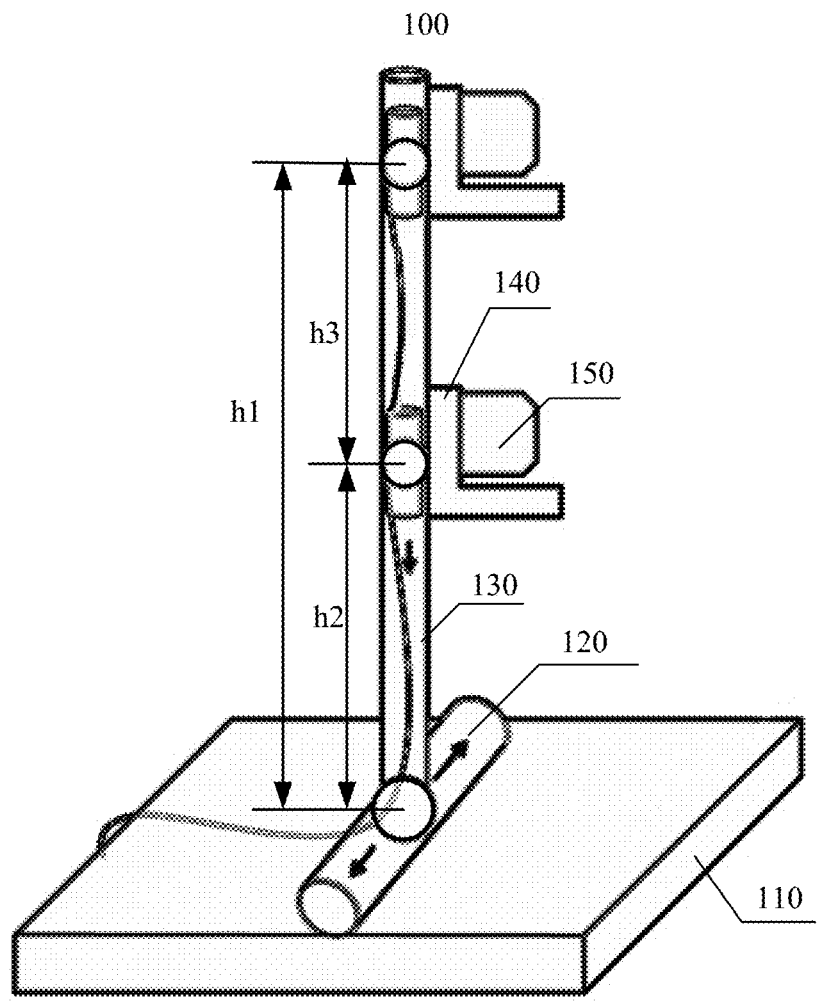
FIG. 5 is an exemplary schematic diagram of an orientational movement of another mechanical arm according to this application.

Exemplarily, as shown in FIG. 5, the control assembly 150 controls the camera assembly 150 to vertically move on the vertical track by a distance h3. The control assembly 150 controls the vertical track to horizontally move on the translation track 120 by a distance 0.

In the second one of two designed structures of the mechanical arm, since the plurality of rotary shafts of the mechanical arm are designed to the vertical track, the structure of the auxiliary photographing device is effectively simplified and manufacturing complexity is reduced.

In some other embodiments, the mechanical arm may also have other designed structures, which is not limited in this embodiment of this application.

Based on the above, the technical solution provided in this embodiment of this application provides an auxiliary photographing device for dyskinesia analysis. The control assembly in the auxiliary photographing device can adjust the position of the camera assembly by controlling the orientational movement of the mechanical arm and control the camera assembly to perform photographing. In the related art, a patient is required to wear a wearable device to obtain motion data of the patient. By virtue of the auxiliary photographing device provided in the embodiments of this application, a patient is required to wear no devices, which reduces a constraint on a motion of the patient, thereby ensuring data authenticity, and further improving the accuracy of analysis and diagnosis results.

In addition, the camera assembly in the auxiliary photographing device provided in this embodiment of this application may be a zoom lens, so that the control assembly may control the zoom lens to perform automatic zoom, thereby improving definition of an image that is taken or a video that is recorded, and reducing fuzziness in a motion video.

Figure 6:
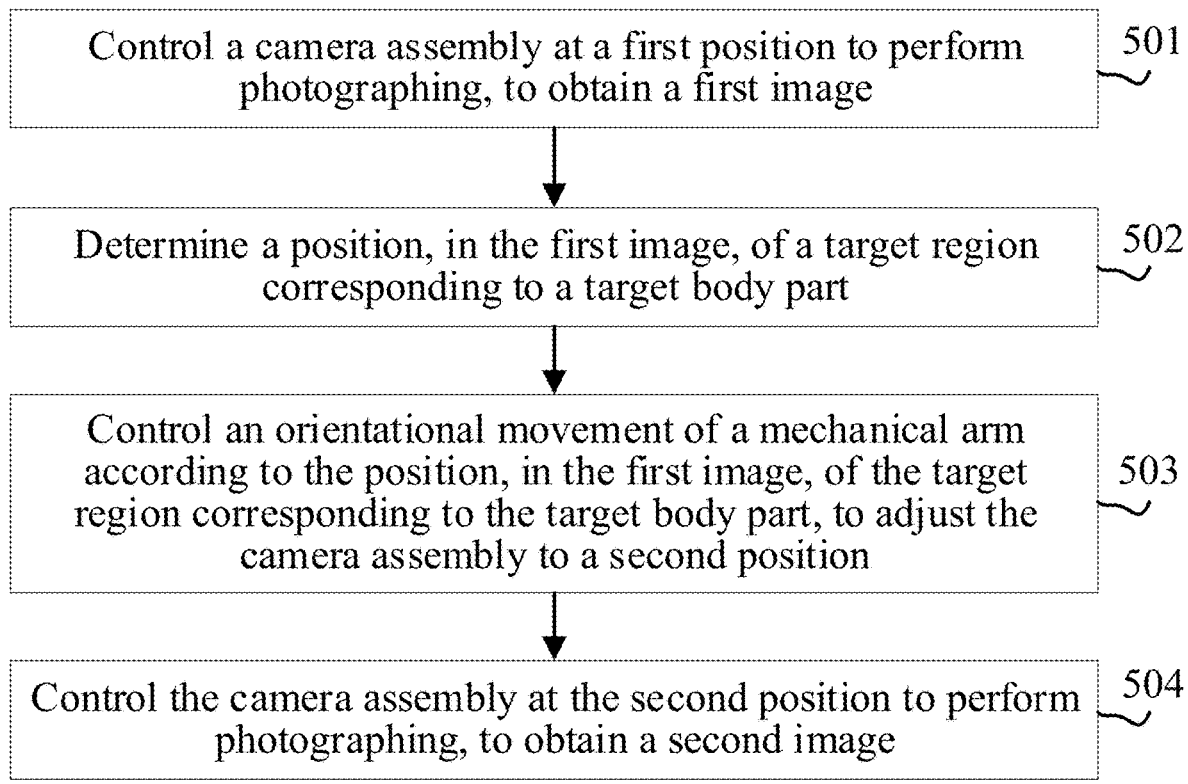
FIG. 6 is a flowchart of a control method for an auxiliary photographing device for dyskinesia analysis according to an embodiment of this application.

FIG. 6 is a flowchart of a control method for an auxiliary photographing device for dyskinesia analysis according to an embodiment of this application. In this embodiment, a description is made mainly by using an example in which the method is applicable to the control assembly in the auxiliary photographing device for dyskinesia analysis described above. The method may include the following steps:

Step 501: Control the camera assembly at a first position to perform photographing, to obtain a first image.

The control assembly may control the camera assembly to perform photographing on a patient having dyskinesia, to obtain the first image. The first image includes a target body part of the patient having dyskinesia. The target body part may be a body part such as a hand, a face, a foot, or the like. The dyskinesia may be the Parkinson's disease, a diffuse lewy body disease, an essential tremor, or hepatolenticular degeneration, which is not limited in this embodiment of this application.

In addition, the first image may be an image or an image frame in a video.

In some embodiments, before controlling the camera assembly at the first position to perform photographing, the control assembly may further control the auxiliary photographing device to prompt the patient about a start of the photographing by using a voice, and may further guide the patient to perform a corresponding action.

The first position may be a position of the camera assembly at an initial start of the auxiliary photographing device, or may be any position in a position adjustment process, which is not limited in this embodiment of this application.

Step 502: Determine a position, in the first image, of a target region corresponding to a target body part.

Upon acquisition of the first image, the control assembly may analyze and process the first image, to determine the position, in the first image, of the target region corresponding to the target body part. The target region corresponding to the target body part is a local region in the first image that includes the target body part.

In some embodiments, a posture recognition model may be invoked to complete the determination of the position, in the first image, of the target region corresponding to the target body part. For detailed description, refer to the following embodiment of FIG. 7, and details are not described herein again.

Step 503: Control the orientational movement of the mechanical arm according to the position, in the first image, of the target region corresponding to the target body part, to adjust the camera assembly to a second position.

Upon determination of the position, in the first image, of the target region corresponding to the target body part, an orientational deviation of a center position of the target region from a center position of the first image may be analyzed. Further, the orientational movement of the mechanical arm may be controlled according to the orientational deviation to adjust the camera assembly to the second position.

The orientational movement of the mechanical arm includes at least one of a horizontal movement and a vertical movement. The control assembly may control the mechanical arm to move only horizontally, only vertically, or both horizontally and vertically.

When the control assembly fails to adjust the camera assembly to an optimal position, the patient may be prompted by using a voice to perform certain posture adjustment.

Step 504: Control the camera assembly at the second position to perform photographing, to obtain a second image.

After the camera assembly is adjusted to the second position, the control assembly may control the camera assembly to perform photographing again, to obtain the second image. The second image includes the target body part. In some embodiments, since the position of the camera assembly is controlled to be adjusted, the target region corresponding to the target body part is in a center position of the second image.

In this embodiment of this application, a center position of an image is a position of a center point of the image. For example, assuming that the image is a rectangular image having a length L and a width W, and a two-dimensional rectangular coordinate system is constructed by using an upper left vertex of the image as an origin, coordinates of the center position of the image may be represented as (L/2, W/2). The target region corresponding to the target body part being in the center position of the second image means that the target region corresponding to the target body part includes the center position of the second image.

In some embodiments, the position of the camera assembly may be adjusted so that the target region corresponding to the target body part is at about a center position of the second image. Here, "about" a center position of an image may be refer to within ±10% of the dimension of the image relative to the center of the image, e.g., for one coordinate along the Length of the image, about the center position is in a range from 0.4 L to 0.6 L, inclusive; and for another coordinate along the Width of the image, about the center position is in a range from 0.4 W to 0.6 W, inclusive.

In some embodiments, the auxiliary photographing device records a motion video of a patient at a desirable angle. The auxiliary photographing device prompts a required action and a description of the action by using a voice, and controls the camera assembly to enable an image taking function or a motion video recording function.

In some embodiments, upon finish of the photographing, the control assembly controls the camera assembly to stop the photographing, prompts the patient to stop the action by using a voice, and automatically saves the image that is taken or the video that is recorded.

Based on the above, in the technical solution provided in this embodiment of this application, the control assembly in the auxiliary photographing device adjusts the camera assembly to a desirable position by controlling the orientational movement of the mechanical arm, and controls the camera assembly to perform photographing. A target region, in the image that is taken, corresponding to the target body part is in a center position of the image. Compared with the related art in which a patient is required to wear a wearable device to obtain motion data of the patient, in this embodiment of this application, the control assembly of the auxiliary photographing device can automatically adjust the position of the camera assembly. On one hand, the patient does not need to wear any device, thereby reducing a constraint on a motion of the patient and ensuring data authenticity. On the other hand, the control assembly controls the camera assembly to adjust the target region corresponding to the target body part to the center position of the image, so that the target region is clearer, and the accuracy of analysis and diagnosis results may be further improved.

Figure 7:
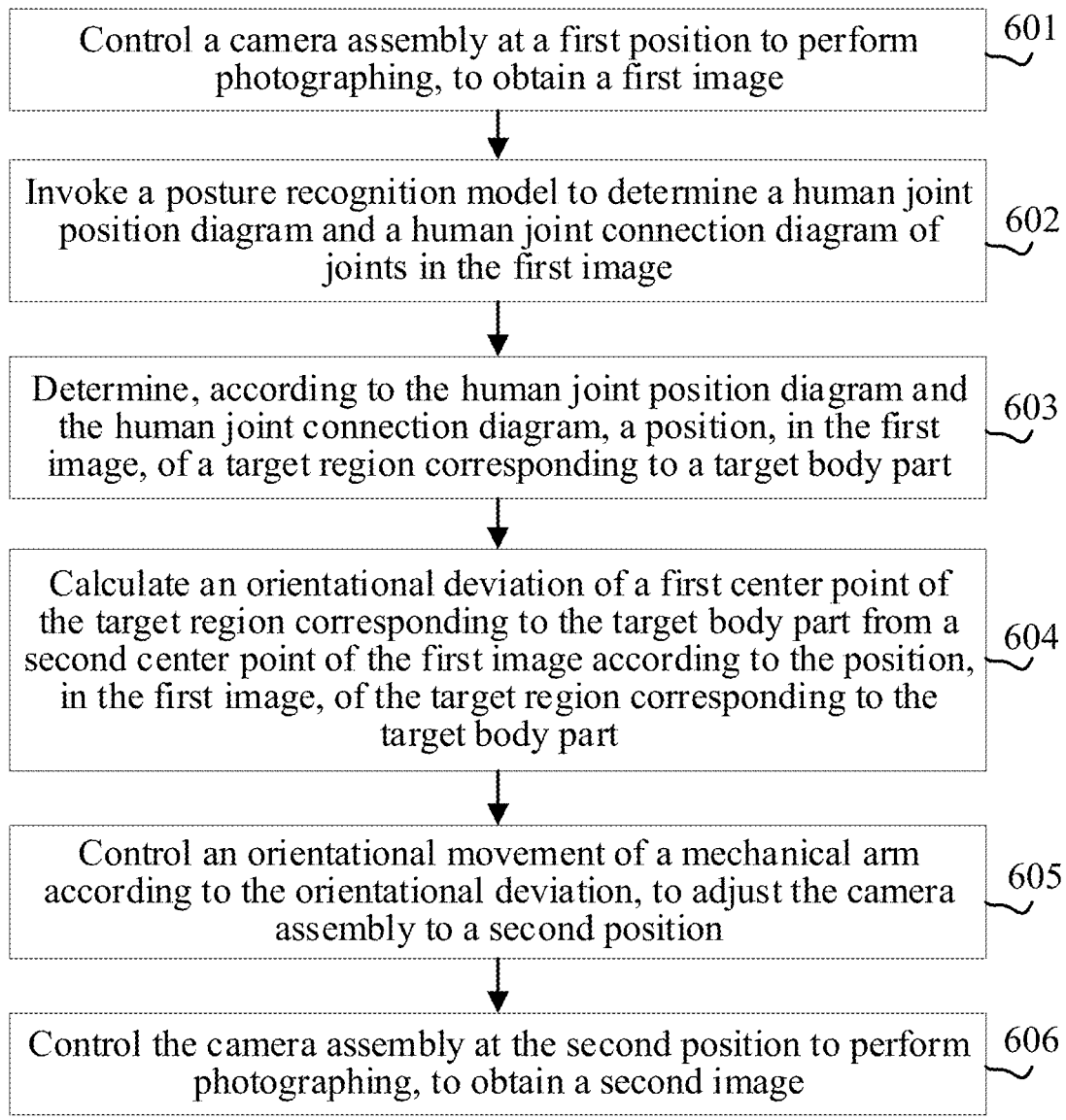
FIG. 7 is a flowchart of a control method for an auxiliary photographing device for dyskinesia analysis according to another embodiment of this application.

FIG. 7 is a flowchart of a control method for an auxiliary photographing device for dyskinesia analysis according to another embodiment of this application. In this embodiment, a description is made mainly by using an example in which the method is applicable to the control assembly in the auxiliary photographing device for dyskinesia analysis described above. The method may include the following steps:

Step 601: Control the camera assembly at a first position to perform photographing, to obtain a first image.

This step is the same as or similar to step 501 in the foregoing embodiment of FIG. 6, and therefore details are not described herein again.

Step 602: Invoke a posture recognition model to determine a human joint position diagram and a human joint connection diagram of joints in the first image.

The control assembly may invoke the posture recognition model to recognize and determine the human joint position diagram and the human joint connection diagram of the joints in the first image. The human joint position diagram is used for representing positions of the human joints in the first image, such as a position of a left shoulder, a position of a left elbow, a position of a left wrist, a position of a nose, a position of a neck, and the like.

Figure 8:
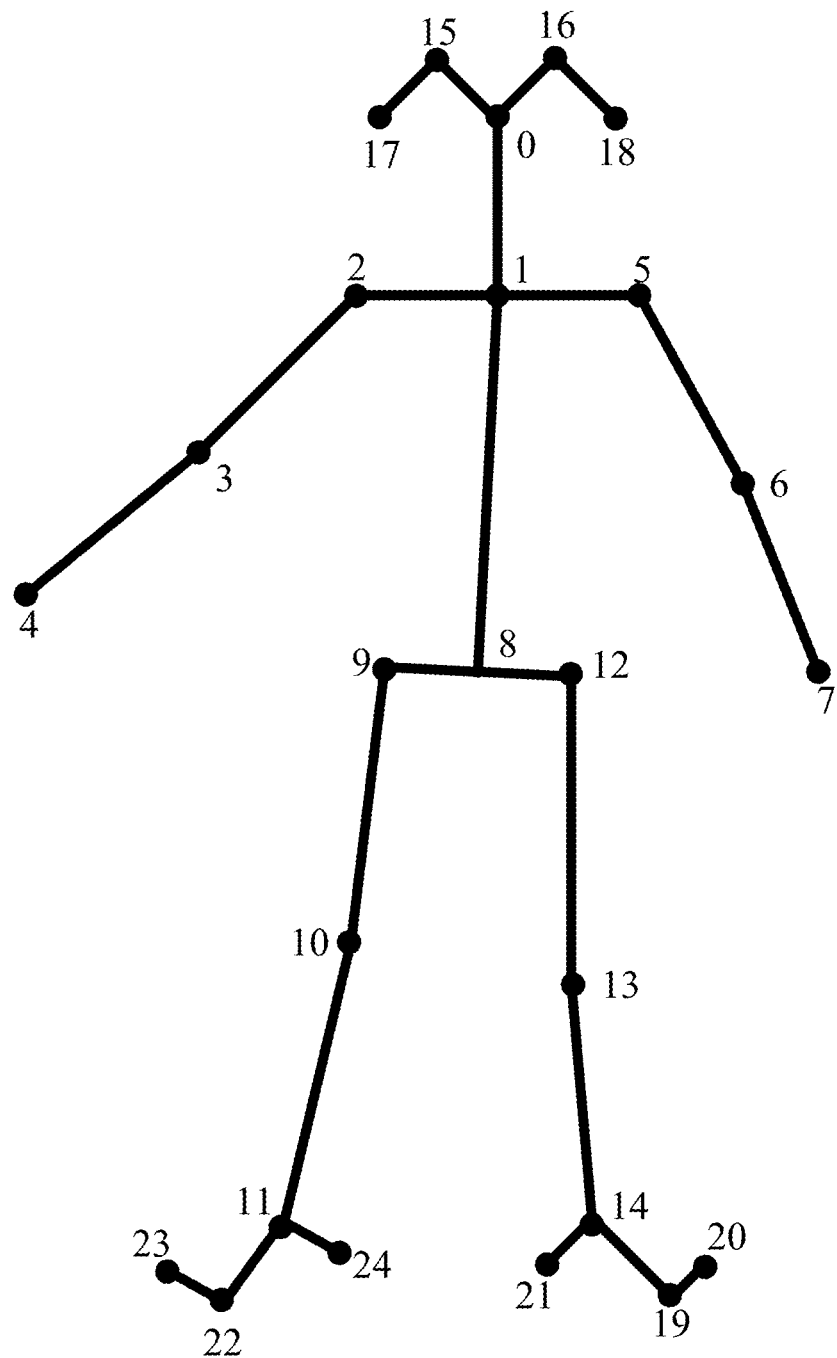
FIG. 8 is an exemplary schematic diagram of a human joint position diagram according to this application.

FIG. 8 is an exemplary schematic diagram of a human joint position diagram. Numbers 0-24 in FIG. 8 respectively correspond to 25 joints of a human body: nose, neck, right shoulder, right elbow, right wrist, left shoulder, left elbow, left wrist, middle hip, right hip, right knee, right ankle, left hip, left knee, left ankle, right eye, left eye, right ear, left ear, left big toe, left small toe, left heel, right big toe, right small toe, and right heel.

The human joint connection diagram is used for representing a connection relationship among the human joints in the first image, such as a line connecting the left shoulder and the left elbow, a line connecting the right shoulder and the right elbow, a line connecting the right elbow and the right wrist, and the like.

Figure 9:
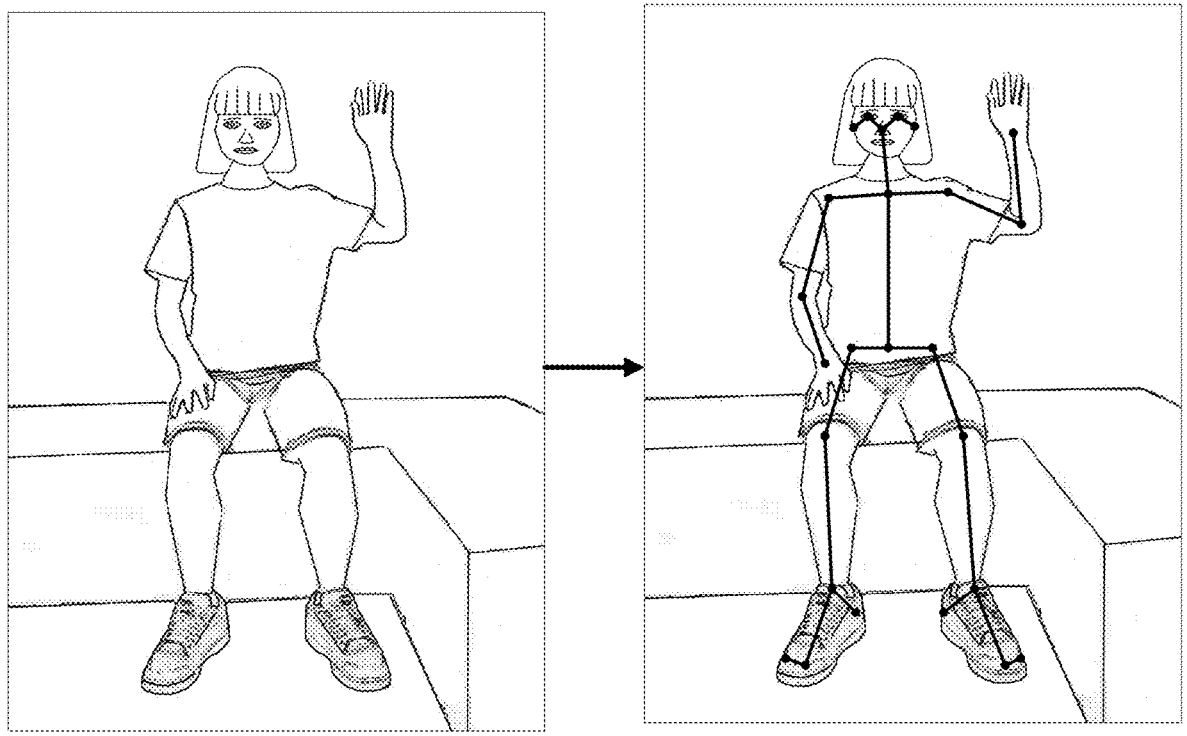
FIG. 9 is an exemplary schematic diagram of a human joint connection diagram according to this application.

FIG. 9 is an exemplary schematic diagram of a human joint connection diagram. (a) in FIG. 9 is the first image. The control assembly may invoke the posture recognition model to determine a human joint connection diagram shown by (b) in FIG. 9.

The posture recognition model may be an end-to-end deep learning model. An input of the model may be the first image, and an output is the human joint position diagram and the human joint connection diagram of the joints in the first image. For description of the posture recognition model, refer to the embodiments provided in FIG. 14 to FIG. 16, and details are not described herein again.

Step 603: Determine, according to the human joint position diagram and the human joint connection diagram, the position, in the first image, of the target region corresponding to the target body part.

Upon acquisition of the human joint position diagram and the human joint connection diagram, the position, in the first image, of the target region corresponding to the target body part may be determined according to the human joint position diagram and the human joint connection diagram.

In some embodiments, the determination of the position, in the first image, of the target region corresponding to the target body part according to the human joint position diagram and the human joint connection diagram may include the following sub-steps:

(1): Determine, according to the human joint position diagram and the human joint connection diagram, a related joint associated with the target body part.

The related joint may be a joint having a connection relationship with the target body part. For example, assuming that the target body part is a hand, the related joint associated with the target body part may be a wrist and an elbow.

(2): Acquire position coordinates of the related joint.

Further, the position coordinates of the related joint may be determined according to the human joint position diagram.

(3): Determine, according to the position coordinates of the related joint, the position, in the first image, of the target region corresponding to the target body part.

Figure 10:
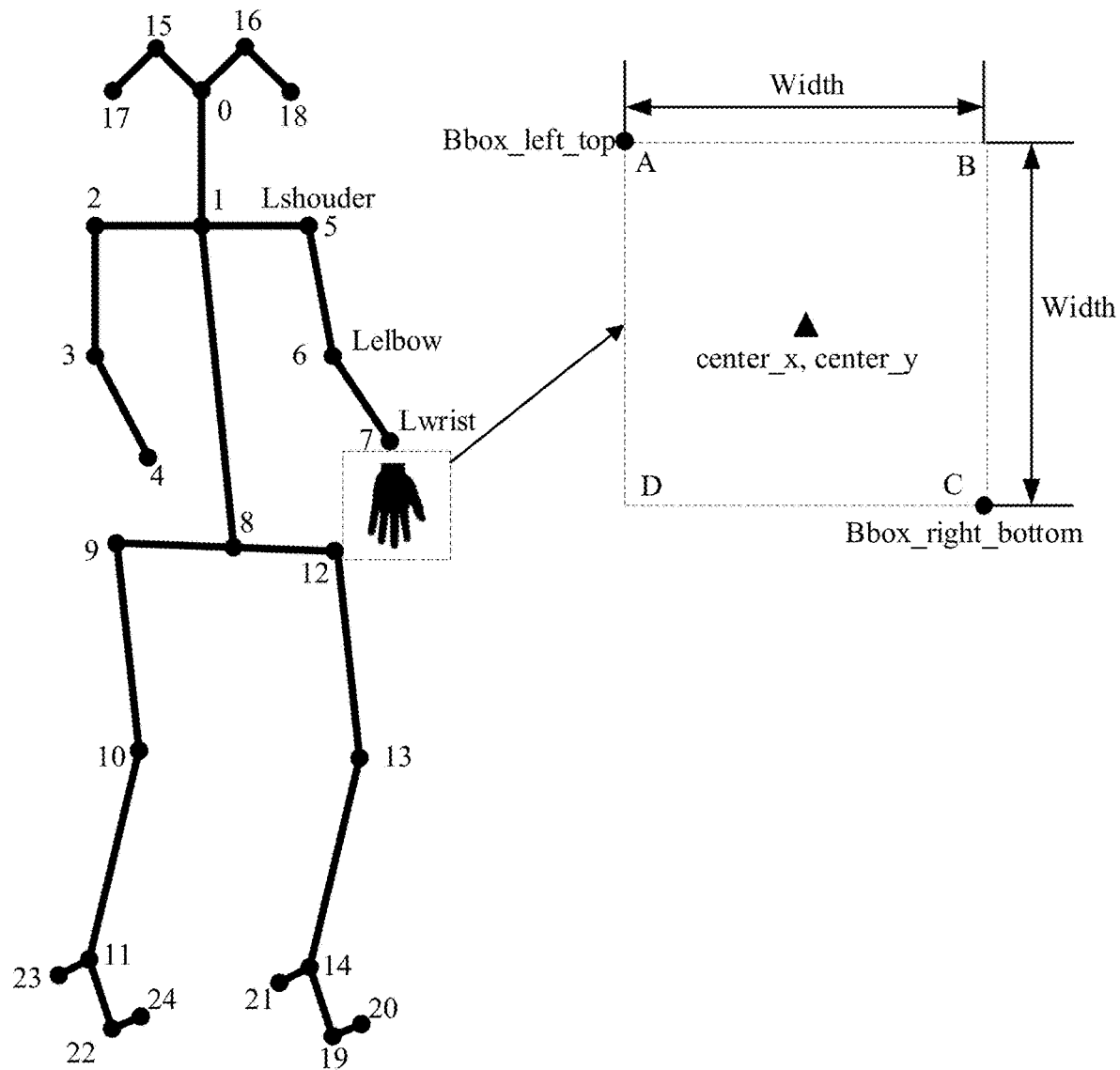
FIG. 10 is an exemplary schematic diagram of determining a target region according to this application.

FIG. 10 is an exemplary schematic diagram of determining a target region. The target body part is a hand and the target region is a hand region, for example. A dashed-line box in the figure represents the hand region. The control assembly may determine that a related joint associated with the hand includes a wrist (a point shown by a number 6 in FIG. 10) and an elbow (a point shown by a number 7 in FIG. 10), and may further acquire position coordinates of the wrist and the elbow. The position coordinates both include an x-axis coordinate and a y-axis coordinate.

The x-axis coordinate may be indexed or represented by [0], and the y-axis coordinate may be indexed or represented by [1]. In other words, the position coordinates of the wrist may be represented as (lwrist[0], lwrist[1]), and the position coordinates of the elbow may be represented as (lelbow[0], lelbow[1]).

According to the position coordinates of the wrist and the elbow and the human joint connection diagram, position coordinates of a center point of the hand region (represented by a black triangle in FIG. 10) may be calculated according to the following equations:

$$center\_x = lwrist[0] + 0.33*(lwrist[0] - lelbow[0]);$$

$$center\_y = lwrist[1] + 0.33*(lwrist[1] - lelbow[1]), \text{ where}$$

center_x represents an x-axis coordinate of the center point of the hand region, and center_y represents a y-axis coordinate of the center point of the hand region. In other words, the coordinates of the center point of the hand region may be represented as (center_x, center_y).

Upon acquisition of the coordinates of the center point of the hand region, expansion is performed toward two sides around the center point to obtain the hand region shown by a dashed-line box ABCD in FIG. 10. A side length of the dashed-line box ABCD may be calculated by using the following equations:

$$Width = 1.5*max(DistanceWristElbow, 0.9*DistanceElbowShoulder);$$

$$DistanceWristElbow = \sqrt{(lwrist[0] - lelbow[0])^2 + (lwrist[1] - lelbow[1])^2};$$

$$DistanceElbowShoulder = \sqrt{(lshoulder[0] - lelbow[0])^2 + (lshoulder[1] - lelbow[1])^2},$$

Width represents the side length of the dashed-line box ABCD, DistanceWristElbow represents a distance between the wrist and the elbow, DistanceElbowShoulder represents a distance between the elbow and a shoulder, lshoulder[0] represents an x-axis coordinate of the shoulder, and lshoulder[1] represents a y-axis coordinate of the shoulder.

Based on the position coordinates of the center point of the hand region and the side length of the dashed-line box, two coordinates of an upper left corner (point A) and a lower right corner (point C) forming the dashed-line box may be calculated according to the following equations:

$$Bbox\_left\_top[0] = center\_x - Width/2;$$

$$Bbox\_left\_top[1] = center\_y - Width/2;$$

$$Bbox\_right\_bottom[0] = center\_x + Width/2;$$

$$Bbox\_right\_bottom[1] = center\_y + Width/2, \text{ where}$$

Bbox_left_top[0] represents an x-axis coordinate of the point A, Bbox_left_top[1] represents a y-axis coordinate of the point A, Bbox_right_bottom[0] represents an x-axis coordinate of the point C, and Bbox_right_bottom[1] represents a y-axis coordinate of the point C.

So far, the final hand region, that is, the target region corresponding to the target body part is obtained.

Step 604: Calculate an orientational deviation of a first center point of the target region corresponding to the target body part from a second center point of the first image according to the position, in the first image, of the target region corresponding to the target body part.

Upon determination of the position, in the first image, of the target region corresponding to the target body part, the first center point of the target region corresponding to the target body part and the second center point of the first image may be determined, and the orientational deviation of the first center point from the second center point may be further calculated.

The orientational deviation may be used for representing a deviation of the target region from the center position of the first image in the first image. The orientational deviation may include a transverse deviation and a longitudinal deviation.

In some embodiments, the calculation of the orientational deviation of the first center point of the target region corresponding to the target body part from the second center point of the first image according to the position, in the first image, of the target region corresponding to the target body part may include the following sub-steps:

(1): Determine position coordinates of the first center point and position coordinates of the second center point.

(2) Determine a transverse deviation distance and a longitudinal deviation distance between the position coordinates of the first center point and the position coordinates of the second center point.

Figure 11:
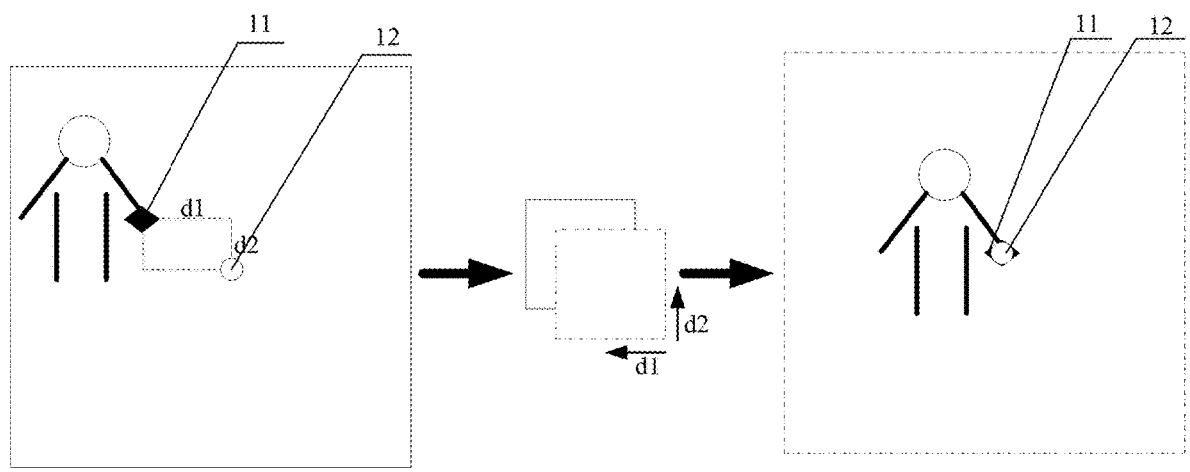
FIG. 11 is an exemplary schematic diagram of adjusting a position of a camera assembly according to this application.

FIG. 11 is an exemplary schematic diagram of adjusting a position of a camera assembly A diamond in FIG. 11 represents a first center point 11 of the target region corresponding to the target body part, and a small hollow circle represents a second center point 12 of the first image. Upon determination of the position coordinates of the first center point and the position coordinates of the second center point, a transverse deviation distance d1 and a longitudinal deviation distance d2 may be obtained.

Step 605: Control the orientational movement of the mechanical arm according to the orientational deviation, to adjust the camera assembly to the second position.

Upon determination of the orientational deviation, the position of the camera assembly may be adjusted according to the orientational deviation.

In some embodiments, the control of the orientational movement of the mechanical arm according to the orientational deviation to adjust the camera assembly to the second position includes: controlling the mechanical arm to horizontally move by the transverse deviation distance and vertically move by the longitudinal deviation distance, to adjust the camera assembly to the second position.

Upon acquisition of the orientational deviation, a movement direction and a movement distance for the mechanical arm of the auxiliary photographing device may be further calculated.

FIG. 3 is an exemplary schematic diagram of an orientational movement of a mechanical arm. It may be learned according to the orientational deviation that the mechanical arm 130 needs to horizontally move by the transverse deviation distance d1 and vertically move by the longitudinal deviation distance d2. The horizontal movement is realized by using the translation track 120, and the vertical movement is realized by using the rotary shaft. As shown in FIG. 3, a length of the rotary shaft is L. Assuming that an angle of the rotary shaft at the first position is $\alpha_0$, and an angle of the rotary shaft after the movement to the second position is $\alpha 1$, an angle $\alpha$ by which the rotary shaft needs to be rotated may be calculated by using the following equation:

$\alpha = \alpha_0 - \alpha_1$, where $\alpha_1 = \sin^{-1}\frac{h_2}{h_1}$; $h_2 = Lg\sin\alpha_0 - d_2$;

h1 represents a height of the third rotary shaft from a horizontal line at the first position, and h2 represents a height of the third rotary shaft from the horizontal line at the second position. The horizontal line is a horizontal line passing through a connection point of the third rotary shaft and the second rotary shaft.

Step 606: Control the camera assembly at the second position to perform photographing, to obtain a second image.

The second image includes the target body part, and the target region corresponding to the target body part is in a center position of the second image.

Figure 12:
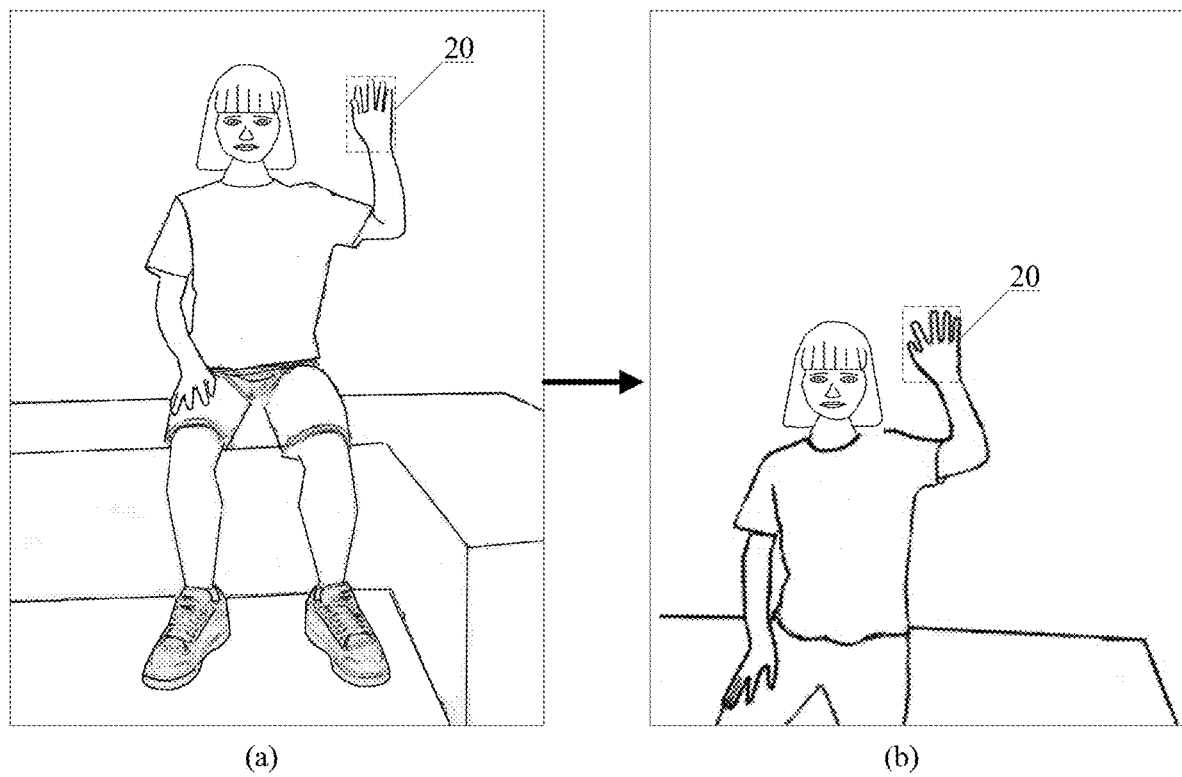
FIG. 12 is an exemplary schematic diagram of a target region after adjustment of a position of a camera assembly according to this application.

Exemplarily, as shown in FIG. 12, the target region corresponding to the target body part is a hand region 20, for example. (a) in FIG. 12 is the first image. In the first image, the hand region 20 is in an upper position of the first image. (b) in FIG. 12 is the second image. In the second image, the hand region 20 is in the center position of the second image.

In some embodiments, when the camera assembly is a zoom lens, before controlling the camera assembly at the second position to perform photographing to obtain the second image, the control assembly may further perform the following steps:

(1): Detect the target body part to determine an aspect ratio of the target region corresponding to the target body part to the first image.

(2): Control, according to the aspect ratio, the camera assembly to adjust a focal length, to adjust the aspect ratio of the target region corresponding to the target body part to the first image.

When the camera assembly is adjusted to the second position, the target region corresponding to the to-be-photographed target body part is in a middle position of the second image. In this case, a specific position and a size of the target region may be further detected, and an aspect ratio of the target region corresponding to the target body part to the first image may be calculated. Further, a focal length of the camera assembly may be adjusted, so that the target region corresponding to the target body part fills the image as fully as possible. In this way, the target region corresponding to the target body part is clearer.

Figure 13:
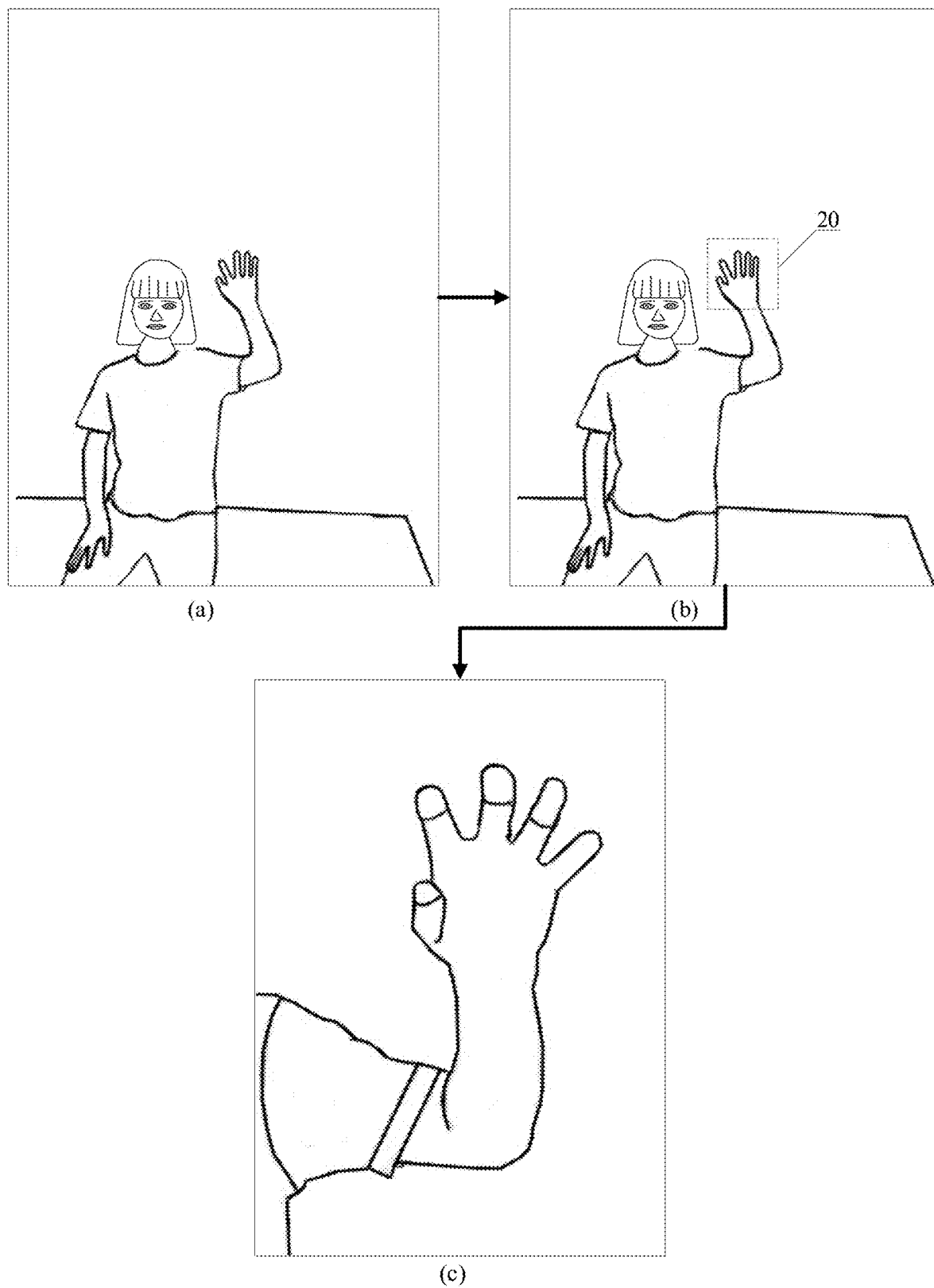
FIG. 13 is an exemplary schematic diagram of a target region after adjustment of a focal length of a camera assembly according to this application.

Exemplarily, as shown in FIG. 13, the target region corresponding to the target body part is a hand region 20, for example. (a) in FIG. 13 shows an image taken when a focal length is not adjusted. It may be learned that, a hand region has a small aspect ratio to the image. (b) in FIG. 13 shows an aspect ratio of a target region corresponding to the target body part to the first image, and a photographing focal length is adjusted according to the aspect ratio. (c) in FIG. 13 shows an image taken after the focal length is adjusted. It may be learned that a hand region 20 has a relatively large aspect ratio to the image, and the hand region is much clearer.

Based on the above, according to the technical solutions provided in the embodiments of this application, the control assembly in the auxiliary photographing device invokes the posture recognition model, determines a position, in the image, of the target region corresponding to the target body part according to an output result of the posture recognition model, further determines an orientational deviation of a center point of the target region from a center point of the image, and adjusts the camera assembly to an optimal position according to the orientational deviation, so that the target region corresponding to the target body part is in a center position of the image. By means of the posture recognition model that is invoked and a related AI algorithm, the auxiliary photographing device can automatically adjust the photographing position, the photographing angle, and the focal length without manual adjustment, avoiding the cumbersome operation of manually adjusting the photographing angle. In this way, time and manpower are saved, and photographing efficiency is improved.

In addition, when the camera assembly is adjusted to the optimal position, the focal length of the camera assembly may be further adjusted, so that the target region corresponding to the target body part fills the image as fully as possible. In this way, the target region corresponding to the target body part is much clearer.

Figure 14:
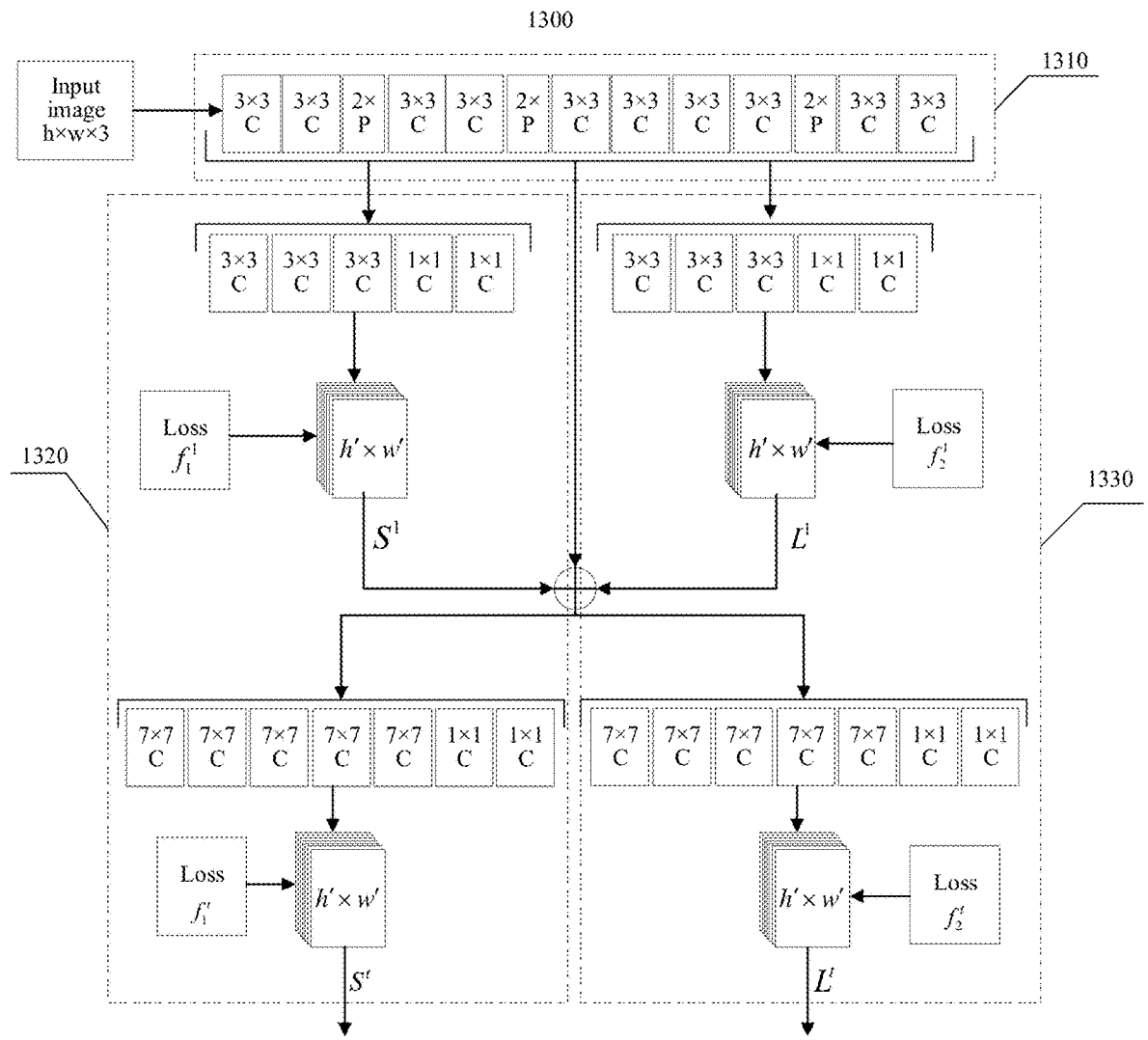
FIG. 14 is an exemplary schematic diagram of a posture recognition model according to this application.

The posture recognition model is described in detail below. FIG. 14 is an exemplary schematic diagram of a posture recognition model. The posture recognition model 1300 includes a feature extraction portion 1310, a position determination portion 1320, and a connection determination portion 1330.

The feature extraction portion 1310 is configured to extract an image feature of the first image. The feature extraction portion may be first ten layers of a VGG19. The image feature may also include at least one of a color feature, a texture feature, a shape feature, and a semantic feature.

After the image feature is extracted, the image features may be inputted to the position determination portion 1320 and the connection determination portion 1330. The position determination portion 1320 is configured to calculate, according to the image feature, confidence of each pixel in the first image belonging to a target joint, to obtain a human joint position diagram of a target joint.

Figure 15:
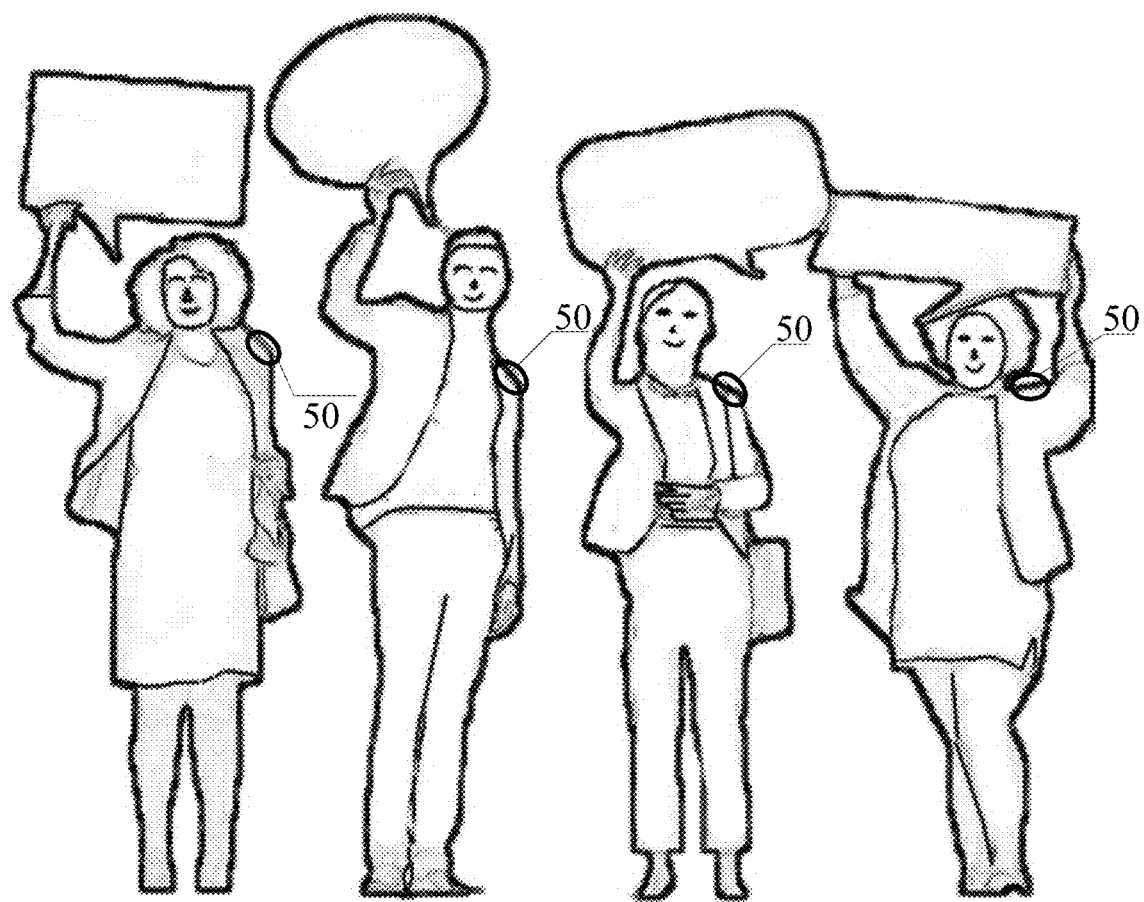
FIG. 15 is an exemplary schematic diagram of a human joint position diagram according to this application.

Exemplarily, as shown in FIG. 15, the position determination portion 1320 may calculate confidence of each of h'×w' pixels belonging to a left shoulder, and convert the confidence to an image display, that is, a human joint position diagram. A region in the figure that is marked by a circle 50 is a brightest region in the figure, that is, the left shoulder.

In some embodiments, the position determination portion 1320 includes t stages. The t stages correspond to t joints. A first stage of the position determination portion 1320 inputs an image feature and outputs a human joint position diagram of a joint. A stage after the first stage inputs the human joint position diagram, a human joint connection diagram, and a feature map that are outputted by the stage previous to the stage.

The connection determination portion 1330 is configured to determine a vector field in the first image according to the image feature, to obtain the human joint connection diagram, the vector field being used for representing a position and a direction of a line connecting the joints.

In some embodiments, the connection determination portion 1330 also includes t stages. The t stages correspond to t joints. A first stage of the connection determination portion 1330 inputs an image feature and outputs a human joint connection diagram of a line connecting any two joints. A stage after the first stage inputs a human joint position diagram, the human joint connection diagram, and a feature map that are outputted by the stage previous to the stage.

Figure 16:
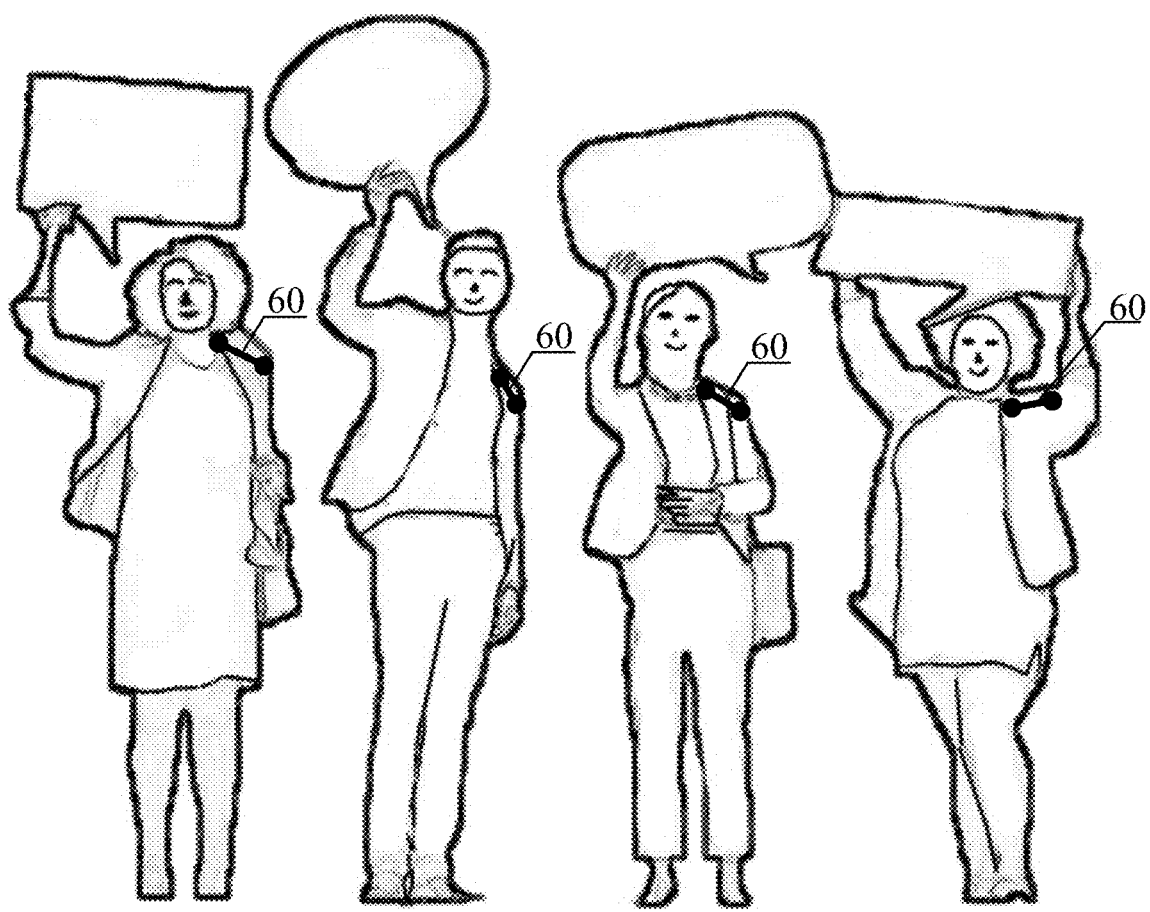
FIG. 16 is an exemplary schematic diagram of a human joint connection diagram according to this application.

Exemplarily, as shown in FIG. 16, the connection determination portion 1330 may connect a neck joint to a left shoulder joint to form a vector field 60. The vector field 60 may indicate a position and a direction of a line connecting the neck joint and the left shoulder joint.

By means of continuous intensive training, the posture recognition model can learn correct positions of body joints from image data, and finally can obtain a human joint position diagram and a human joint connection diagram of each joint.

Based on the above, by means of the technical solution provided in this embodiment of this application, the posture recognition model is invoked to acquire the human joint position diagram and the human joint connection diagram, so as to further determine the target region corresponding to the target body part. By means of the posture recognition model, the accuracy of determining a position of the target region corresponding to the target body part can be improved.

In addition, in the posture recognition model provided in this embodiment of this application, the extraction of the image feature and the prediction of the human joint position diagram and the human joint connection diagram are independent of each other, improving the accuracy of a prediction result.

Figure 17:
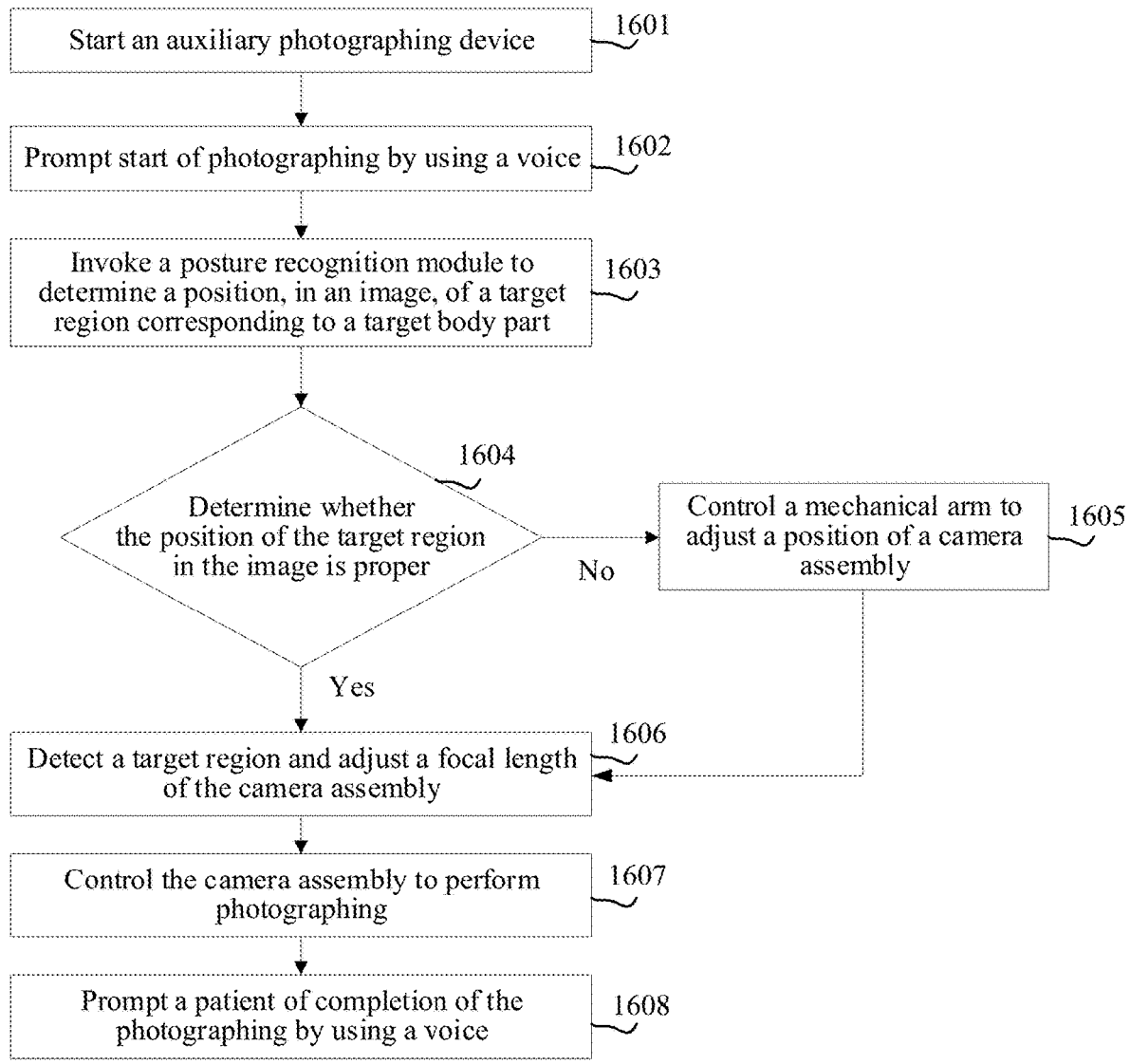
FIG. 17 is an exemplary flowchart of a control method for an auxiliary photographing device for dyskinesia analysis according to this application.

FIG. 17 is an exemplary flowchart of a control method for an auxiliary photographing device for dyskinesia analysis. In this embodiment, a description is made mainly by using an example in which the method is applicable to the control assembly in the auxiliary photographing device for dyskinesia analysis described above.

Upon start of the auxiliary photographing device in 1601, the control assembly may control the auxiliary photographing device to prompt the patient to start photographing by using a voice in 1602. Next, the control assembly may control the camera assembly to perform photographing. Then the control assembly acquires an image returned by the camera assembly, and then invokes the posture recognition model to detect a position of a body joint of a patient, and determines a position of a target region (such as a hand region) corresponding to the target body part in the image in 1603. The control assembly may determine whether the position of the target region in the image is proper in 1604. If not, the control assembly obtains a horizontal movement distance and a vertical movement distance of the mechanical arm by means of calculation and analysis, and further automatically adjusts the position of the camera assembly in 1605 to ensure that an adjusted target region is in the center position of the image. Next, the control assembly may detect the target region to obtain a smallest region that can cover the entire target body part, and the focal length of the camera assembly is adjusted in 1606, so that the target region appears completely in the image as large as possible. Finally, the control assembly may control the camera assembly to perform photographing, record a motion video of a specific action of the patient in 1607, and starts counting. The control assembly completes the recording of the video according to a set photographing time, prompts the patient to stop the action, and prompts the patient of completion of the photographing by using a voice in 1608. The control assembly automatically names and saves the video, and prepares to perform photographing of a next video.

Figure 18:
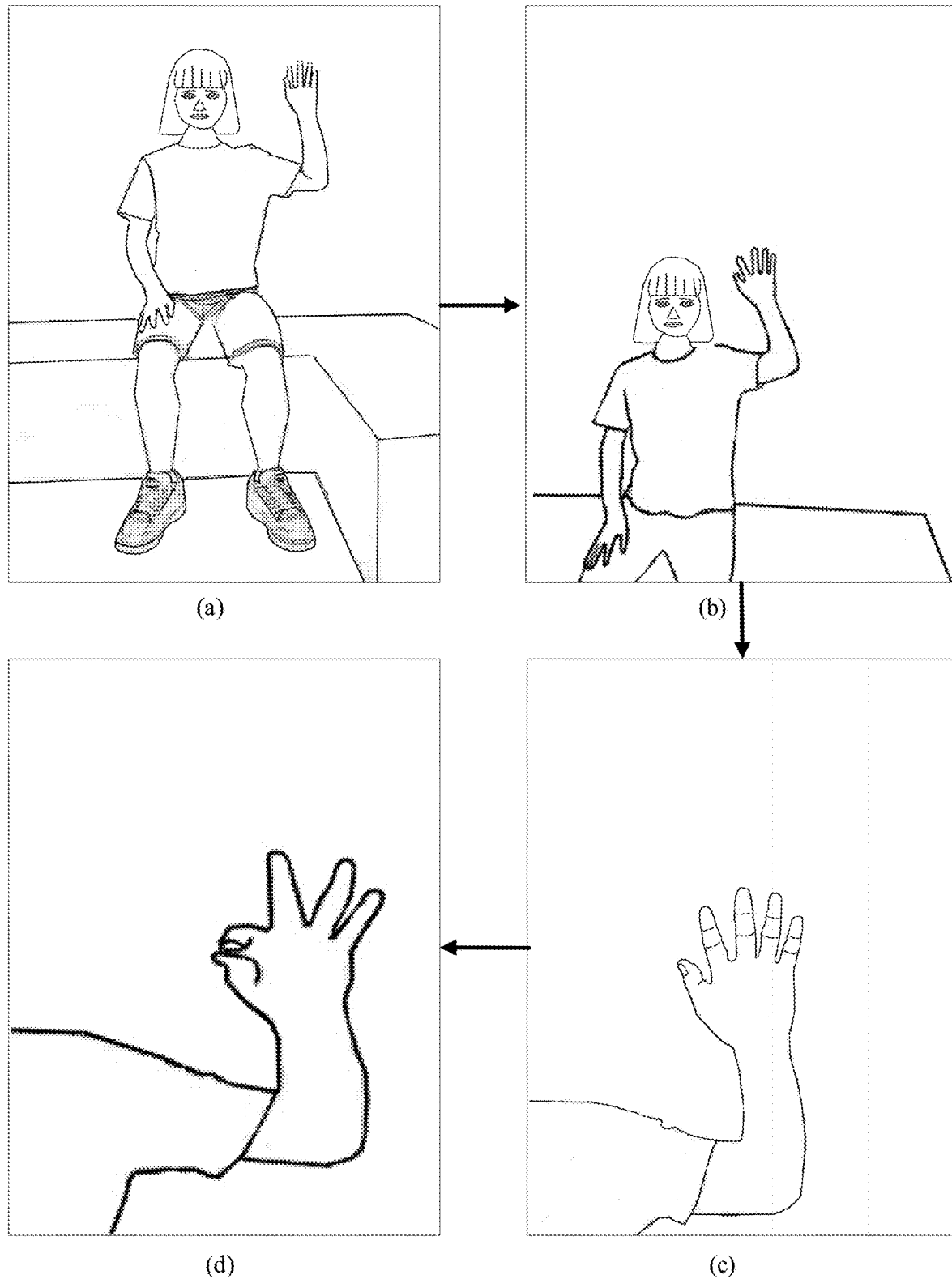
FIG. 18 is an exemplary schematic diagram of a beneficial effect of a solution according to this application.

FIG. 18 is an exemplary schematic diagram of a beneficial effect of the solution according to this application. (a) in FIG. 18 shows a first image taken by the camera assembly at a first position. In the first image, a hand region is located in an upper region. Next, the control assembly controls the orientational movement of the mechanical arm to adjust the camera assembly to a second position, and controls the camera assembly to perform photographing to obtain a second image. As shown in (b) of FIG. 18, in the second image, the hand region is in a center position of the second image. Next, the control assembly may adjust the focal length of the camera assembly, so that a target region corresponding to the target body part fills the image as fully as possible. As shown in (c) of FIG. 18, finally, the control assembly records a video of a specific motion of a hand at the focal length at the second position, and the hand region in the obtained video is much clearer.

The auxiliary photographing device provided in this application is applicable to a video photographing stage of a motion video analysis technology to realize autonomous and intelligent photographing of a corresponding motion video. By means of an AI algorithm, the auxiliary photographing device first automatically locates a moving part (such as a hand, a face, or a foot) of a target body according to a photographing requirement, calculates an optimal photographing angle of the corresponding part, automatically adjusts the position of the camera so that the moving part is at a center of the picture, automatically adjusts the focal length of the camera so that a video that is recorded is much clearer, and finally obtains a high-quality motion video for further video analysis and obtains accurate data for analysis and research of dyskinesia under a clinic condition.

Apparatus embodiments of this application are described below, which may be used for performing the method embodiments of this application. For details not disclosed in the apparatus embodiments of this application, refer to the method embodiments of this application.

Figure 19:
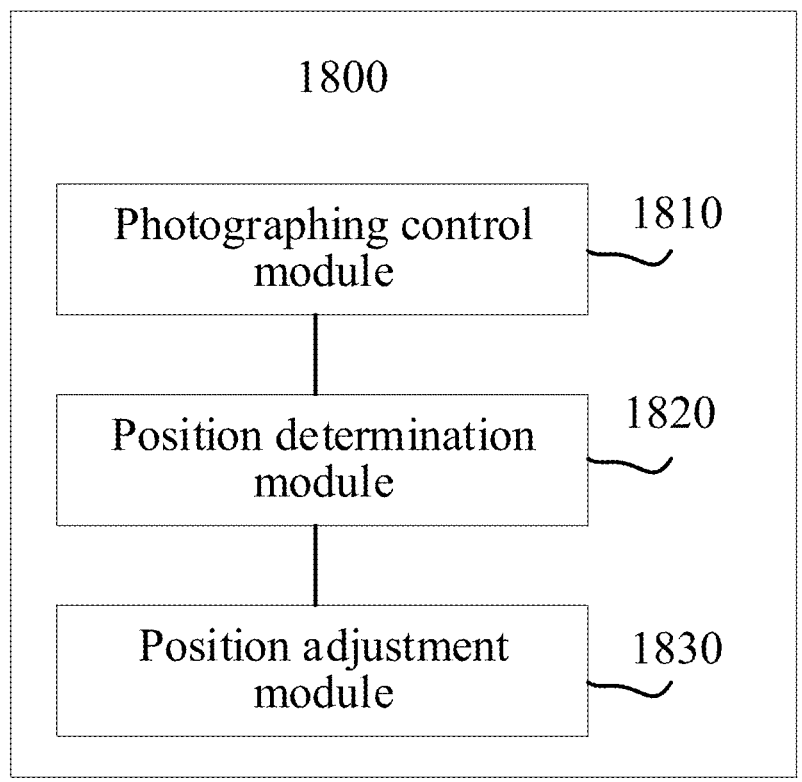
FIG. 19 is a block diagram of a control apparatus for an auxiliary photographing device for dyskinesia analysis according to an embodiment of this application.

FIG. 19 is a block diagram of a control apparatus for an auxiliary photographing device for dyskinesia analysis according to an embodiment of this application. The apparatus has a function of realizing the above method example, and the function may be realized by hardware or by hardware executing corresponding software. The apparatus may be the control assembly described above, or may be disposed on the control assembly. The apparatus 1800 may include a photographing control module 1810, a position determination module 1820, and a position adjustment module 1830.

The photographing control module 1810 is configured to control the camera assembly at a first position to perform photographing, to obtain a first image, the first image including a target body part of a patient having dyskinesia.

The position determination module 1820 is configured to determine a position, in the first image, of a target region corresponding to the target body part.

The position adjustment module 1830 is configured to control an orientational movement of the mechanical arm according to the position of the target region in the first image, to adjust the camera assembly to a second position.

The photographing control module 1810 is configured to control the camera assembly at the second position to perform photographing, to obtain a second image, the second image including the target body part.

In the present disclosure, a unit may refer to a software unit, a hardware unit, or a combination thereof. A software unit may include a computer program or part of the computer program that has a predefined function and works together with other related parts to achieve a predefined goal, such as those functions described in this disclosure. A hardware unit may be implemented using processing circuitry and/or memory configured to perform the functions described in this disclosure. Each unit can be implemented using one or more processors (or processors and memory). Likewise, a processor (or processors and memory) can be used to implement one or more units. Moreover, each unit can be part of an overall unit that includes the functionalities of the unit. The description here also applies to the term unit and other equivalent terms.

In the present disclosure, a module may refer to a software module, a hardware module, or a combination thereof. A software module may include a computer program or part of the computer program that has a predefined function and works together with other related parts to achieve a predefined goal, such as those functions described in this disclosure. A hardware module may be implemented using processing circuitry and/or memory configured to perform the functions described in this disclosure. Each module can be implemented using one or more processors (or processors and memory). Likewise, a processor (or processors and memory) can be used to implement one or more modules. Moreover, each module can be part of an overall module that includes the functionalities of the module. The description here also applies to the term module and other equivalent terms.

Based on the above, in the technical solution provided in this embodiment of this application, the control assembly in the auxiliary photographing device adjusts the camera assembly to a desirable position by controlling the orientational movement of the mechanical arm, and controls the camera assembly to perform photographing. A target region, in the image that is taken, corresponding to the target body part is in a center position of the image. Compared with the related art in which a patient is required to wear a wearable device to obtain motion data of the patient, in this embodiment of this application, the control assembly of the auxiliary photographing device can automatically adjust the position of the camera assembly. On one hand, the patient does not need to wear any device, thereby reducing a constraint on a motion of the patient and ensuring data authenticity. On the other hand, the control assembly controls the camera assembly to adjust the target region corresponding to the target body part to the center position of the image, so that the target region is clearer, and the accuracy of analysis and diagnosis results may be further improved.

Figure 20:
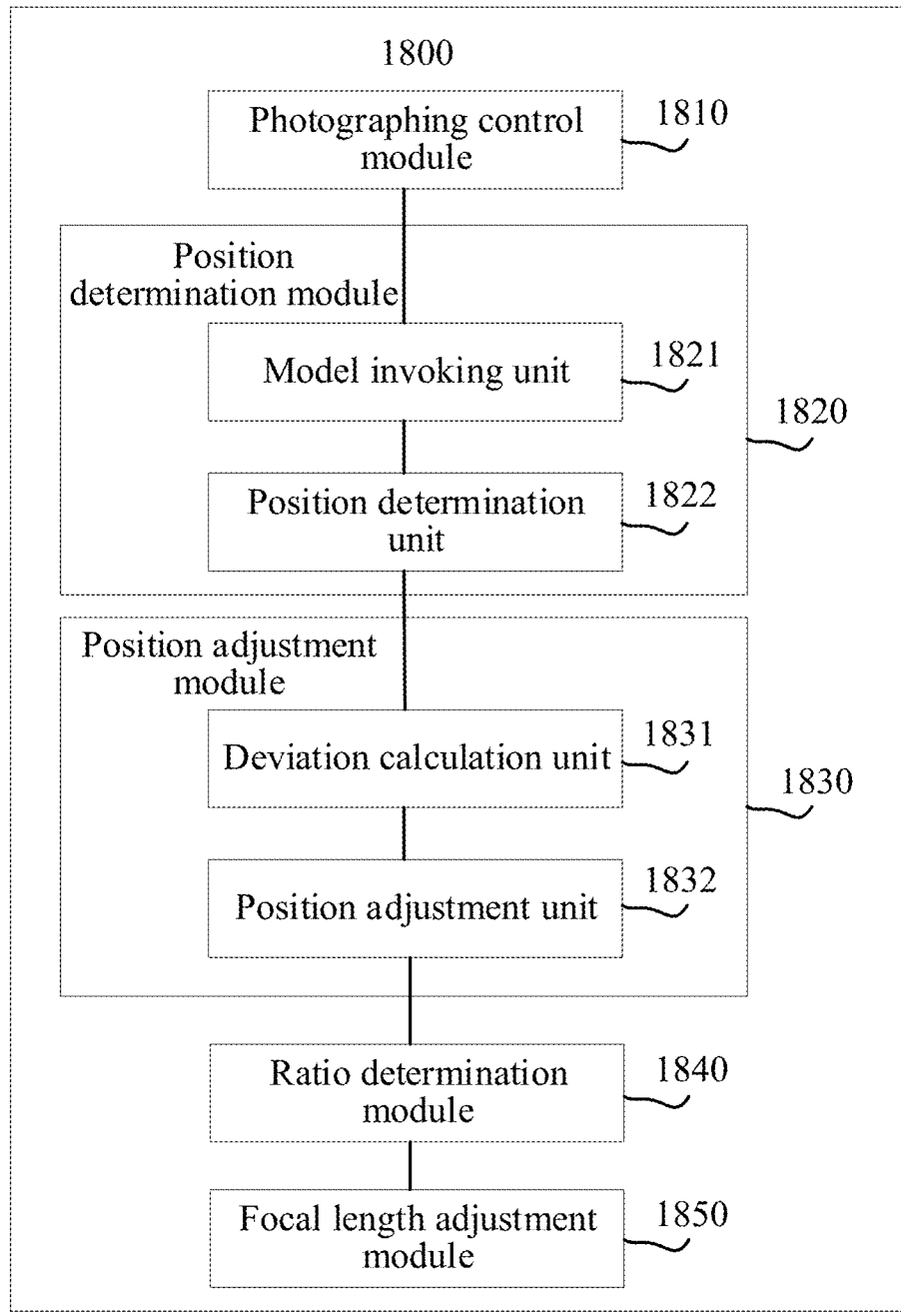
FIG. 20 is a block diagram of a control apparatus for an auxiliary photographing device for dyskinesia analysis according to another embodiment of this application.

In some embodiments, as shown in FIG. 20, the position determination module 1820 includes:

a model invoking unit 1821, configured to invoke a posture recognition model to determine a human joint position diagram and a human joint connection diagram of joints in the first image, the human joint position diagram being used for representing positions of the human joints in the first image, and the human joint connection diagram being used for representing a connection relationship among the human joints in the first image; and a position determination unit 1822, configured to determine, according to the human joint position diagram and the human joint connection diagram, the position, in the first image, of the target region corresponding to the target body part.

In some possible designs, the posture recognition model includes a feature extraction portion, a position determination portion, and a connection determination portion. The feature extraction portion is configured to extract an image feature of the first image. The position determination portion is configured to calculate, according to the image feature, confidence of each pixel in the first image belonging to a target joint, to obtain a human joint position diagram of the target joint. The connection determination portion is configured to determine a vector field in the first image according to the image feature, to obtain the human joint connection diagram, the vector field being used for representing a position and a direction of a line connecting the joints.

In some possible designs, the position determination unit 1822 is configured to determine, according to the human joint position diagram and the human joint connection diagram, a related joint associated with the target body part, acquire position coordinates of the related joint, and determine, according to the position coordinates of the related joint, the position, in the first image, of the target region corresponding to the target body part.

In some possible designs, as shown in FIG. 20, the position adjustment module 1830 includes:

a deviation calculation unit 1831, configured to calculate an orientational deviation of a first center point of the target region corresponding to the target body part from a second center point of the first image according to the position, in the first image, of the target region corresponding to the target body part; and a position adjustment unit 1832, configured to control the orientational movement of the mechanical arm according to the orientational deviation, to adjust the camera assembly to the second position.

In some possible designs, the deviation calculation unit 1831 is configured to determine position coordinates of the first center point and position coordinates of the second center point, and determine a transverse deviation distance and a longitudinal deviation distance between the position coordinates of the first center point and the position coordinates of the second center point.

The position adjustment unit 1832 is configured to control the mechanical arm to horizontally move by the transverse deviation distance and vertically move by the longitudinal deviation distance, to adjust the camera assembly to the second position.

In some possible designs, as shown in FIG. 20, the apparatus 1800 further includes a ratio determination module 1840 and a focal length adjustment module 1850.

The ratio determination module 1840 is configured to detect the target body part to determine an aspect ratio of the target region corresponding to the target body part to the first image.

The focal length adjustment module 1850 is configured to control, according to the aspect ratio, the camera assembly to adjust a focal length, to adjust the aspect ratio of the target region corresponding to the target body part to the first image.

When the apparatus provided in the foregoing embodiments implements functions of the apparatus, the division of the foregoing functional modules is merely an example for description. In the practical application, the functions may be assigned to and completed by different functional modules according to the requirements, that is, the internal structure of the device is divided into different functional modules, to implement all or some of the functions described above. In addition, the apparatus and method embodiments provided in the foregoing embodiments belong to the same concept. For the specific implementation process, reference may be made to the method embodiments, and details are not described herein again.

Figure 21:
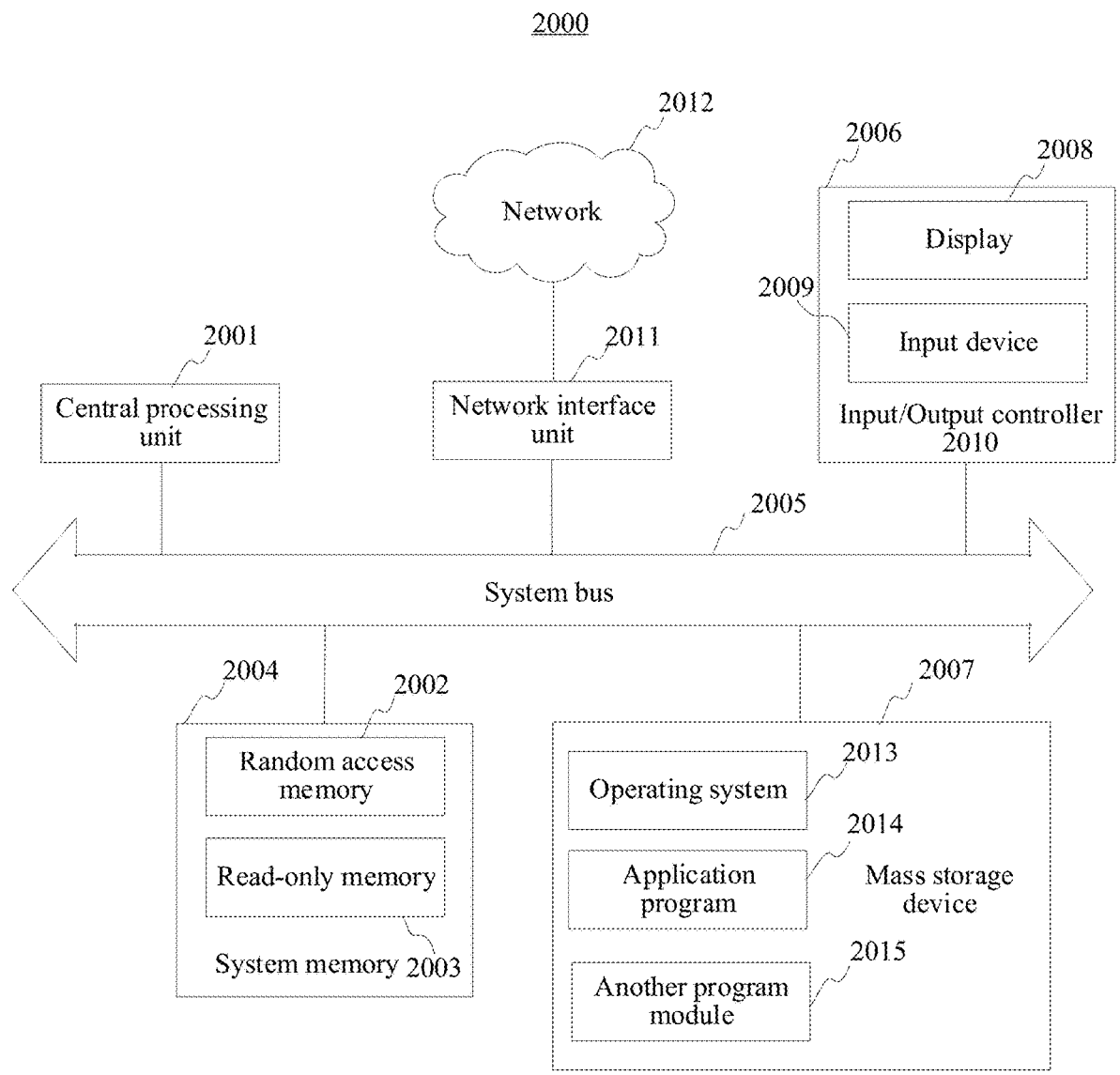
FIG. 21 is a schematic structural diagram of a control assembly according to an embodiment of this application.

FIG. 21 is a schematic structural diagram of a control assembly according to an embodiment of this application. The control assembly is configured to perform the control method for an auxiliary photographing device for dyskinesia analysis provided in the foregoing embodiment.

Specifically, the control assembly 2000 includes a central processing unit (CPU) 2001, a system memory 2004 including a random access memory (RAM) 2002 and a read only memory (ROM) 2003, and a system bus 2005 connecting the system memory 2004 and the CPU 2001. The control assembly 2000 further includes a basic input/output (I/O) system 2006 for facilitating information transmission between various devices in a computer and a mass storage device 2007 configured to store an operating system 2013, an application program 2014, and another program module 2012.

The basic I/O system 2006 includes a display 2008 configured to display information and an input device 2009 such as a mouse or a keyboard for a user to input information. The display 2008 and the input device 2009 are both connected to the CPU 2001 through an I/O controller 2010 connected to the system bus 2005. The basic I/O system 2006 may further include the I/O controller 2010 for receiving and processing inputs from a plurality of other devices such as a keyboard, a mouse, an electronic stylus, or the like. Similarly, the I/O controller 2010 further provides an output to a display screen, a printer, or other types of output devices.

The mass storage device 2007 is connected to the CPU 2001 through a mass storage controller (not shown) connected to the system bus 2005. The mass storage device 2007 and an associated computer-readable medium thereof provide non-volatile storage for the control assembly 2000. That is, the mass storage device 2007 may include a computer-readable medium (not shown) such as a hard disk or a compact disc ROM (CD-ROM) drive.

Without loss of generality, the computer-readable medium may include a computer storage medium and a communication medium. The computer-storage medium includes volatile and non-volatile media, and removable and non-removable media implemented by using any method or technology used for storing information such as computer-readable instructions, data structures, program modules, or other data. The computer storage medium includes a RAM, a ROM, an EPROM, an EEPROM, a flash memory, or other solid-state storage technique, a CD-ROM, a DVD, or other optical storage, a magnetic cassette, a magnetic tape, a magnetic disk storage, or other magnetic storage device. Certainly, a person skilled in the art may learn that the computer storage medium is not limited to the above. The foregoing system memory 2004 and mass storage device 2007 may be collectively referred to as a memory.

According to various embodiments of this application, the control assembly 2000 may be further connected to a remote computer on a network by using a network such as the Internet for running. In other words, the control assembly 2000 may be connected to a network 2012 by using a network interface unit 2011 connected to the system bus 2005, or may be connected to other types of networks or remote computer systems (not shown) by using the network interface unit 2011.

The memory further includes at least one instruction, at least one program, a code set, or an instruction set. The at least one instruction, the at least one program, the code set, or the instruction set is stored in the memory and is configured to be executed by one or more processors to perform the foregoing control method for an auxiliary photographing device for dyskinesia analysis.

In an exemplary embodiment, a computer-readable storage medium is further provided. The computer-readable storage medium stores at least one instruction, at least one program, a code set, or an instruction set which, when executed by a processor, performs the foregoing control method for an auxiliary photographing device for dyskinesia analysis.

In an exemplary embodiment, a computer program product is further provided. The computer program product, when executed by a processor, is used to perform the foregoing control method for an auxiliary photographing device for dyskinesia analysis.

It is to be understood that "plurality of" mentioned in this specification means two or more. And/or describes an association relationship between associated objects and means that three relationships may exist. For example, A and/or B may represent the following three cases: Only A exists, both A and B exist, and only B exists. The character "/" generally indicates an "or" relationship between the associated objects.

The foregoing descriptions are merely exemplary embodiments of this application, but are not intended to limit this application. Any modification, equivalent replacement, or improvement made within the spirit and principle of this application shall fall within the protection scope of this application.

What is claimed is:

1. An apparatus for controlling an auxiliary photographing device for dyskinesia analysis, the apparatus comprising:
    a memory storing instructions; and
    a processor in communication with the memory, wherein, when the processor executes the instructions, the processor is configured to cause the apparatus to perform:
        controlling a camera assembly of the auxiliary photographing device at a first position to perform photographing, to obtain a first image, the first image comprising a target body part of a patient having dyskinesia,
        determining, in the first image, a position of a target region corresponding to the target body part,
        controlling an orientational movement of a mechanical arm of the auxiliary photographing device according to the position of the target region, to adjust the camera assembly to a second position,
        detecting the target body part to determine an aspect ratio of the target region to the first image,
        controlling, according to the aspect ratio, the camera assembly to adjust a focal length, to adjust the aspect ratio of the target region to the first image, and
        controlling the camera assembly at the second position to perform photographing, to obtain a second image, the second image comprising the target body part.

2. The apparatus according to claim 1, wherein the determining the position of the target region comprises:
    invoking a posture recognition model to determine a human joint position diagram and a human joint connection diagram in the first image, the human joint position diagram representing positions of human joints in the first image, and the human joint connection diagram representing a connection relationship among the human joints in the first image; and
    determining, according to the human joint position diagram and the human joint connection diagram, the position of the target region.

3. The apparatus according to claim 2, wherein the posture recognition model is configured to perform:
    extracting an image feature of the first image;
    calculating, according to the image feature, confidence of each pixel in the first image belonging to a target joint, to obtain a human joint position diagram of the target joint; and
    determining a vector field in the first image according to the image feature, to obtain the human joint connection diagram, the vector field being used for representing a position and a direction of a line connecting the human joints.

4. The apparatus according to claim 2, wherein the determining, according to the human joint position diagram and the human joint connection diagram, the position of the target region, comprises:
 determining, according to the human joint position diagram and the human joint connection diagram, a related joint associated with the target body part;
 acquiring position coordinates of the related joint; and
 determining, according to the position coordinates of the related joint, the position of the target region.

5. The apparatus according to claim 1, wherein the controlling the orientational movement of the mechanical arm according to the position of the target region, to adjust the camera assembly to the second position, comprises:
 calculating an orientational deviation of a first center point of the target region from a second center point of the first image according to the position of the target region; and
 controlling the orientational movement of the mechanical arm according to the orientational deviation, to adjust the camera assembly to the second position.

6. The apparatus according to claim 5, wherein:
 the calculating the orientational deviation of the first center point of the target region from the second center point of the first image according to the position of the target region, comprises:
  determining position coordinates of the first center point and position coordinates of the second center point, and
  determining a transverse deviation distance and a longitudinal deviation distance between the first center point and the second center point based on the position coordinates of the first center point and the position coordinates of the second center point; and
 the controlling the orientational movement of the mechanical arm according to the orientational deviation, to adjust the camera assembly to the second position, comprises:
  controlling the mechanical arm to horizontally move by the transverse deviation distance and vertically move by the longitudinal deviation distance, to adjust the camera assembly to the second position.

7. A method for controlling an auxiliary photographing device for dyskinesia analysis, the method comprising:
 controlling, by a device comprising a memory storing instructions and a processor in communication with the memory, a camera assembly of the auxiliary photographing device at a first position to perform photographing, to obtain a first image, the first image comprising a target body part of a patient having dyskinesia;
 determining, by the device in the first image, a position of a target region corresponding to the target body part;
 controlling, by the device, an orientational movement of a mechanical arm of the auxiliary photographing device according to the position of the target region, to adjust the camera assembly to a second position;
 detecting, by the device, the target body part to determine an aspect ratio of the target region to the first image;
 controlling, by the device according to the aspect ratio, the camera assembly to adjust a focal length, to adjust the aspect ratio of the target region to the first image; and
 controlling, by the device, the camera assembly at the second position to perform photographing, to obtain a second image, the second image comprising the target body part.

8. The method according to claim 7, wherein the determining the position of the target region comprises:
 invoking, by the device, a posture recognition model to determine a human joint position diagram and a human joint connection diagram in the first image, the human joint position diagram representing positions of human joints in the first image, and the human joint connection diagram representing a connection relationship among the human joints in the first image; and
 determining, by the device according to the human joint position diagram and the human joint connection diagram, the position of the target region.

9. The method according to claim 8, wherein the posture recognition model is configured to perform:
 extracting an image feature of the first image;
 calculating, according to the image feature, confidence of each pixel in the first image belonging to a target joint, to obtain a human joint position diagram of the target joint; and
 determining a vector field in the first image according to the image feature, to obtain the human joint connection diagram, the vector field being used for representing a position and a direction of a line connecting the human joints.

10. The method according to claim 8, wherein the determining, according to the human joint position diagram and the human joint connection diagram, the position of the target region comprises:
 determining, according to the human joint position diagram and the human joint connection diagram, a related joint associated with the target body part;
 acquiring position coordinates of the related joint; and
 determining, according to the position coordinates of the related joint, the position of the target region.

11. The method according to claim 7, wherein the controlling the orientational movement of the mechanical arm according to the position of the target region, to adjust the camera assembly to the second position comprises:
 calculating an orientational deviation of a first center point of the target region from a second center point of the first image according to the position of the target region; and
 controlling the orientational movement of the mechanical arm according to the orientational deviation, to adjust the camera assembly to the second position.

12. The method according to claim 11, wherein:
 the calculating the orientational deviation of the first center point of the target region from the second center point of the first image according to the position of the target region comprises:
  determining position coordinates of the first center point and position coordinates of the second center point, and
  determining a transverse deviation distance and a longitudinal deviation distance between the first center point and the second center point based on the position coordinates of the first center point and the position coordinates of the second center point; and
 the controlling the orientational movement of the mechanical arm according to the orientational deviation, to adjust the camera assembly to the second position comprises:
  controlling the mechanical arm to horizontally move by the transverse deviation distance and vertically move by the longitudinal deviation distance, to adjust the camera assembly to the second position.

13. A non-transitory computer-readable storage medium, storing computer-readable instructions, wherein, the computer-readable instructions, when executed by a processor, are configured to cause the processor to perform:
- controlling a camera assembly of an auxiliary photographing device at a first position to perform photographing, to obtain a first image, the first image comprising a target body part of a patient having dyskinesia;
- determining, in the first image, a position of a target region corresponding to the target body part;
- controlling an orientational movement of a mechanical arm of the auxiliary photographing device according to the position of the target region, to adjust the camera assembly to a second position;
- detecting the target body part to determine an aspect ratio of the target region to the first image;
- controlling, according to the aspect ratio, the camera assembly to adjust a focal length, to adjust the aspect ratio of the target region to the first image; and
- controlling the camera assembly at the second position to perform photographing, to obtain a second image, the second image comprising the target body part.

14. The non-transitory computer-readable storage medium according to claim 13, wherein, the determining the position of the target region comprises:
- invoking a posture recognition model to determine a human joint position diagram and a human joint connection diagram in the first image, the human joint position diagram representing positions of human joints in the first image, and the human joint connection diagram representing a connection relationship among the human joints in the first image; and
- determining, according to the human joint position diagram and the human joint connection diagram, the position of the target region.

15. The non-transitory computer-readable storage medium according to claim 14, wherein the posture recognition model is configured to perform:
- extracting an image feature of the first image;
- calculating, according to the image feature, confidence of each pixel in the first image belonging to a target joint, to obtain a human joint position diagram of the target joint; and
- determining a vector field in the first image according to the image feature, to obtain the human joint connection diagram, the vector field being used for representing a position and a direction of a line connecting the human joints.

16. The non-transitory computer-readable storage medium according to claim 14, wherein, the determining, according to the human joint position diagram and the human joint connection diagram, the position of the target region, comprises:
- determining, according to the human joint position diagram and the human joint connection diagram, a related joint associated with the target body part;
- acquiring position coordinates of the related joint; and
- determining, according to the position coordinates of the related joint, the position of the target region.

17. The non-transitory computer-readable storage medium according to claim 13, wherein, the controlling the orientational movement of the mechanical arm according to the position of the target region, to adjust the camera assembly to the second position, comprises:
- calculating an orientational deviation of a first center point of the target region from a second center point of the first image according to the position of the target region; and
- controlling the orientational movement of the mechanical arm according to the orientational deviation, to adjust the camera assembly to the second position.

18. The non-transitory computer-readable storage medium according to claim 17, wherein:
- the calculating the orientational deviation of the first center point of the target region from the second center point of the first image according to the position of the target region, comprises:
  - determining position coordinates of the first center point and position coordinates of the second center point, and
  - determining a transverse deviation distance and a longitudinal deviation distance between the first center point and the second center point based on the position coordinates of the first center point and the position coordinates of the second center point; and
- the controlling the orientational movement of the mechanical arm according to the orientational deviation, to adjust the camera assembly to the second position, comprises:
  - controlling the mechanical arm to horizontally move by the transverse deviation distance and vertically move by the longitudinal deviation distance, to adjust the camera assembly to the second position.

* * * * *